(12) United States Patent
Brodnick

(10) Patent No.: US 10,004,414 B2
(45) Date of Patent: Jun. 26, 2018

(54) DETECTING STIMULUS PULSES

(71) Applicant: APN HEALTH, LLC, Pewaukee, WI (US)

(72) Inventor: Donald Brodnick, Cedarburg, WI (US)

(73) Assignee: APN Health, LLC, Pewaukee, WI (US)

( * ) Notice: Subject to any disclaimer, the term of this patent is extended or adjusted under 35 U.S.C. 154(b) by 2 days.

(21) Appl. No.: 15/019,247

(22) Filed: Feb. 9, 2016

(65) Prior Publication Data

US 2017/0224242 A1    Aug. 10, 2017

(51) Int. Cl.
| | |
|---|---|
| *A61B 5/00* | (2006.01) |
| *A61B 5/04* | (2006.01) |
| *A61B 5/0402* | (2006.01) |
| *A61N 1/37* | (2006.01) |

(52) U.S. Cl.
CPC ........ *A61B 5/04017* (2013.01); *A61B 5/0402* (2013.01); *A61B 5/7217* (2013.01); *A61N 1/371* (2013.01)

(58) Field of Classification Search
CPC .......................... A61B 5/04017; A61B 5/0402
USPC ........................................................ 600/510
See application file for complete search history.

(56) References Cited

U.S. PATENT DOCUMENTS

| | | | |
|---|---|---|---|
| 4,105,023 | A  | 8/1978  | Marchese et al. |
| 4,149,527 | A  | 4/1979  | Naylor et al. |
| 4,664,116 | A  | 5/1987  | Shaya et al. |
| 7,471,977 | B2 | 12/2008 | Zinser et al. |
| 2015/0305640 | A1 | 10/2015 | Reinke |
| 2015/0305642 | A1 | 10/2015 | Reinke |

*Primary Examiner* — Nadia A Mahmood
(74) *Attorney, Agent, or Firm* — Jansson Munger McKinley & Kirby Ltd.

(57) ABSTRACT

A method for detecting a stimulus pulse by using two or more electrical signals derived from a living body, the method comprising the following steps: (a) for each electrical signal, digitizing the signal with an analog-to-digital converter to produce a sampled signal $S_k$; (b) for each signal $S_k$ at a sample time $t_i$, computing a primary difference $\Delta_{kp}(t_i)=abs[S_k(t_i)-S_k(t_{i-p})]$; (c) determining the minimum value of all of the computed differences, such minimum being a detector output $D(t_i)$; (d) comparing the detector output $D(t_i)$ with a detection threshold; and (e) indicating that a stimulus pulse has been detected when the detector output $D(t_i)$ is above the detection threshold.

29 Claims, 17 Drawing Sheets

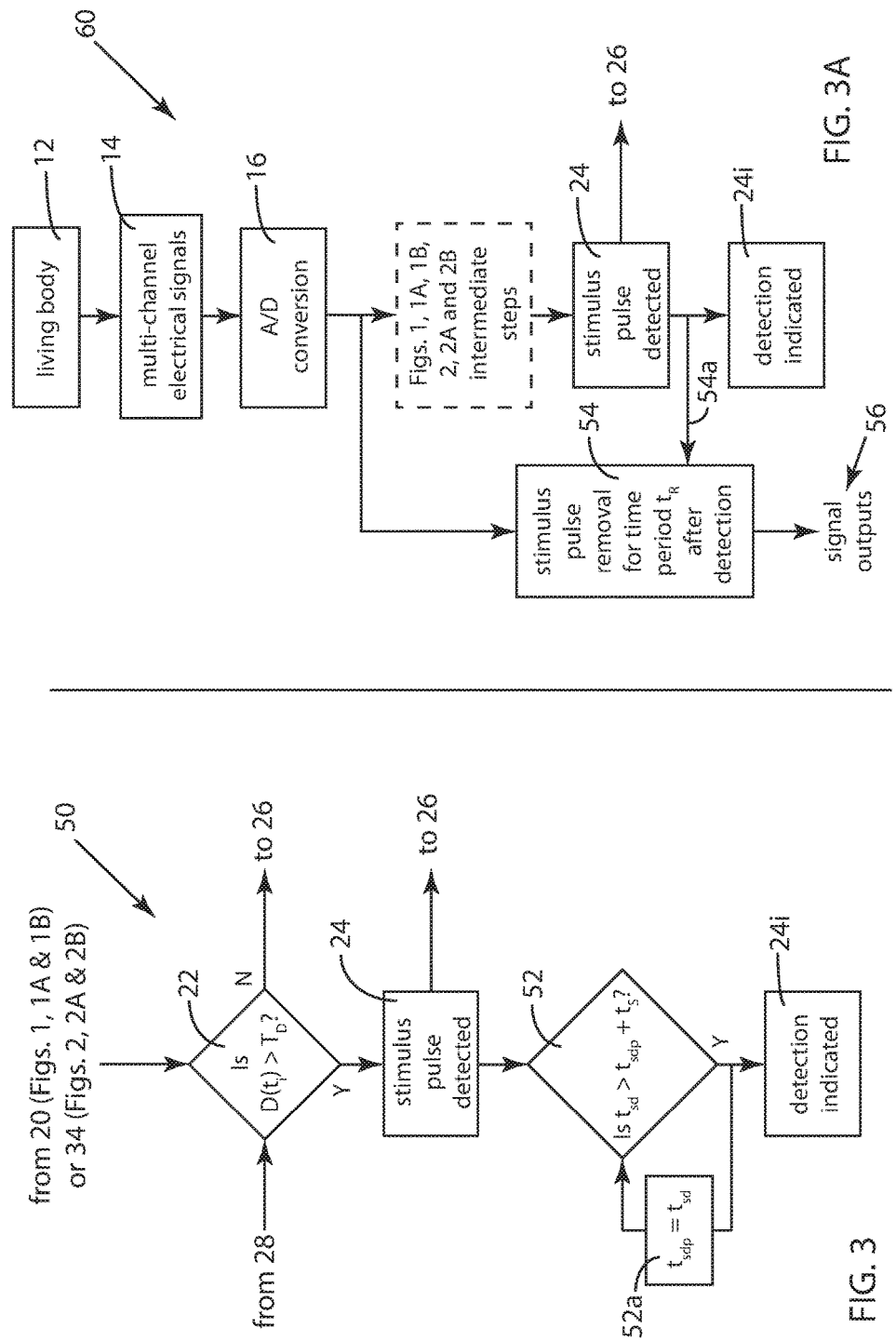

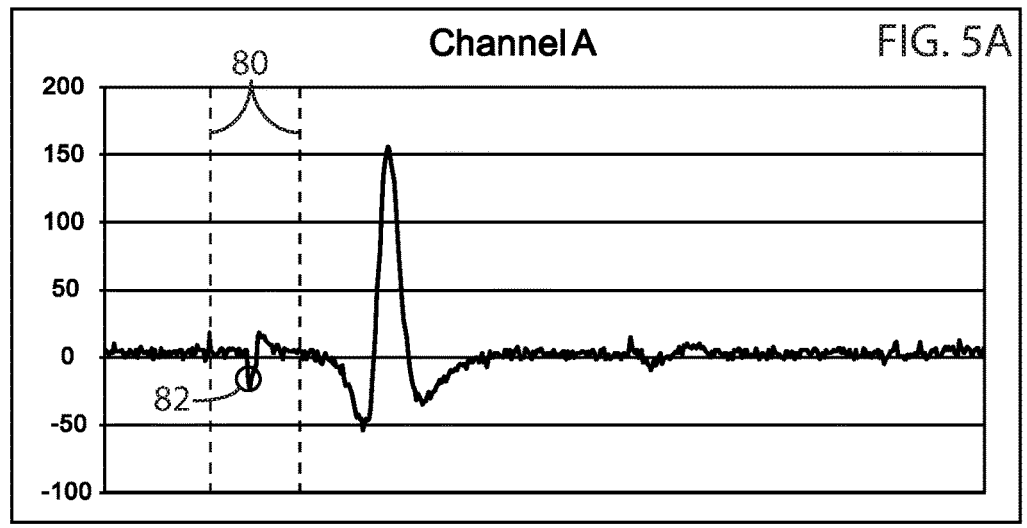
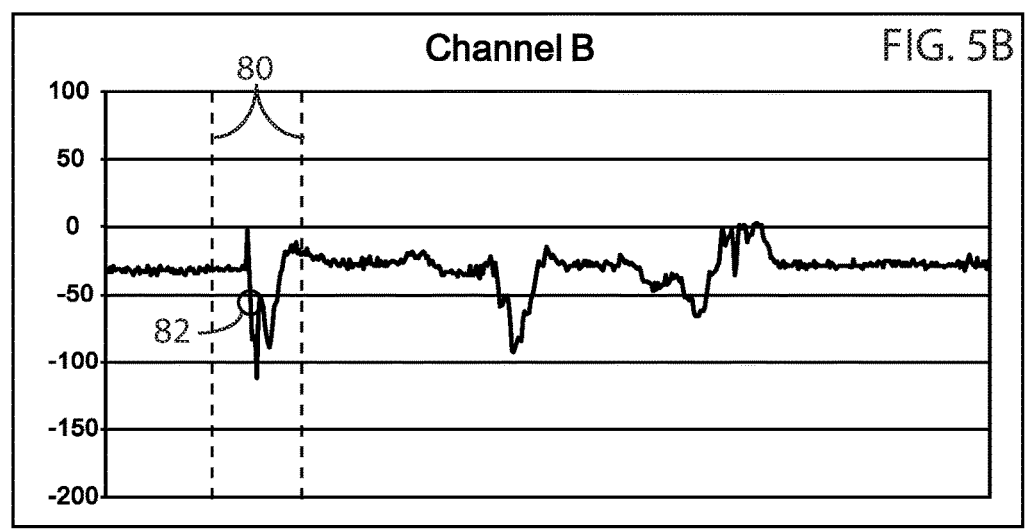

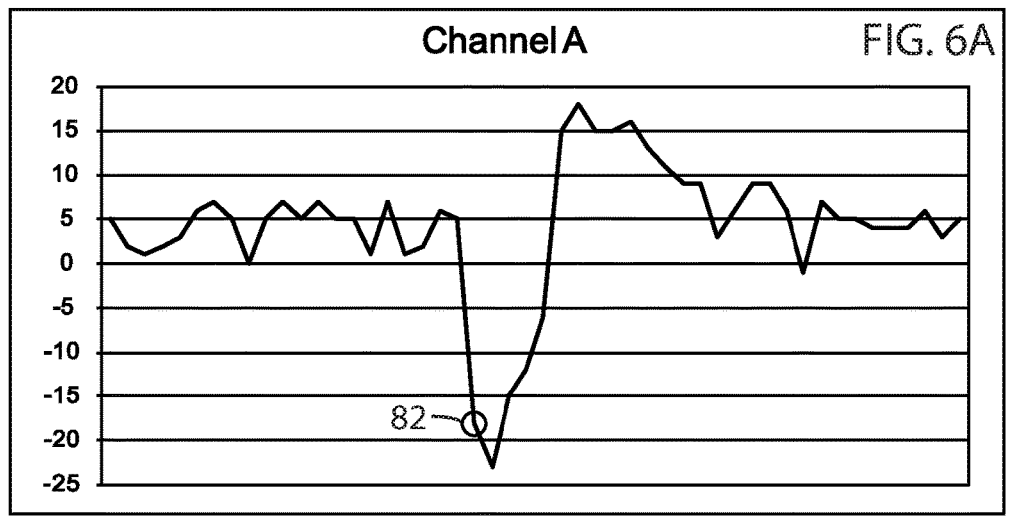
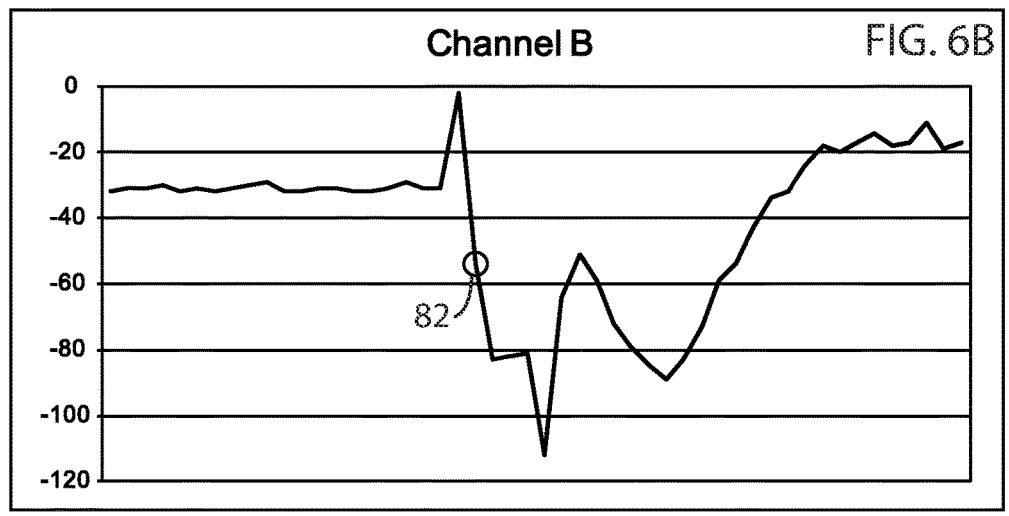

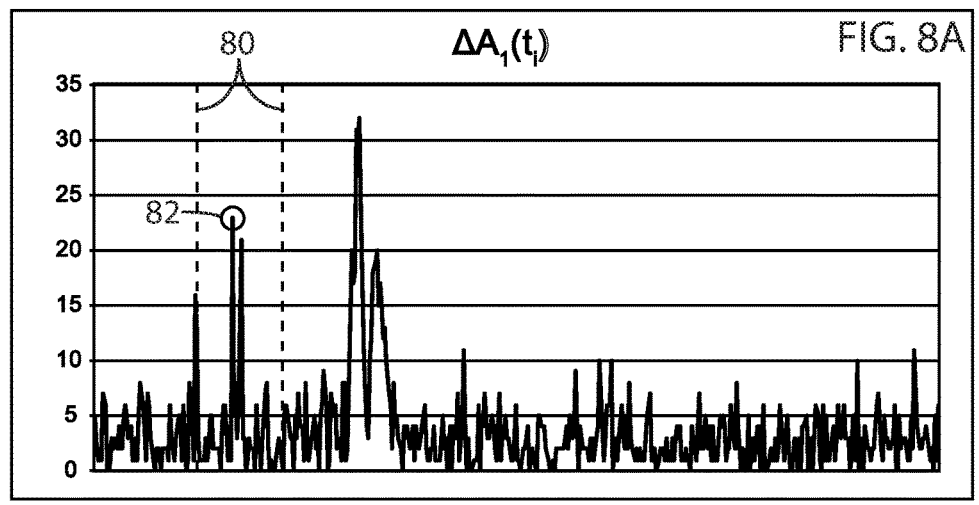
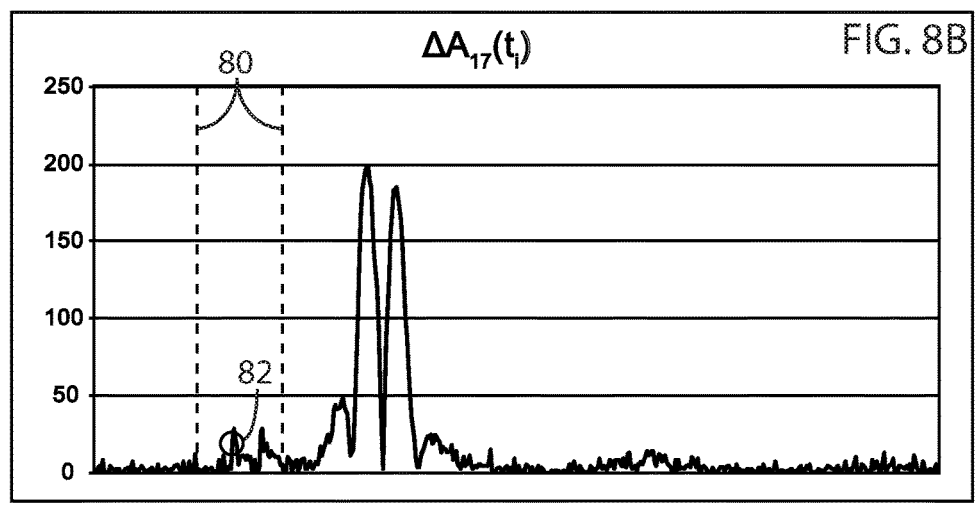
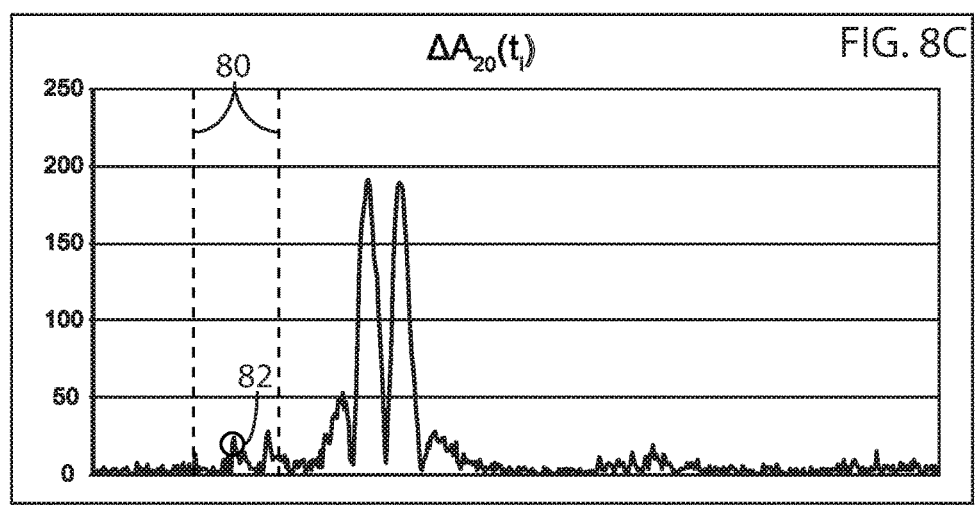

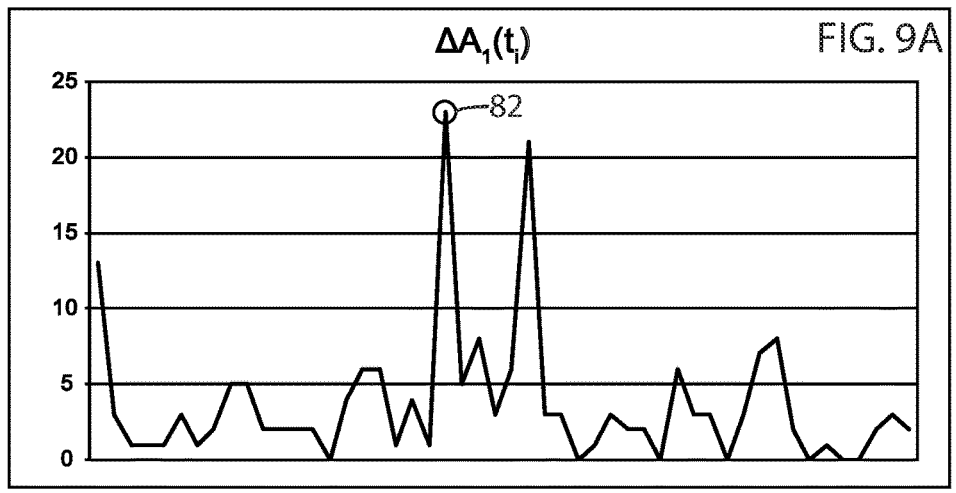
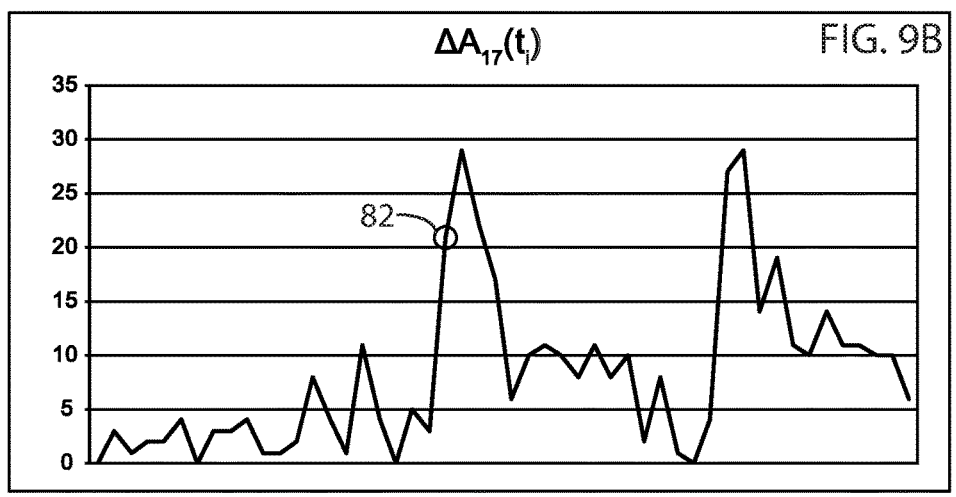
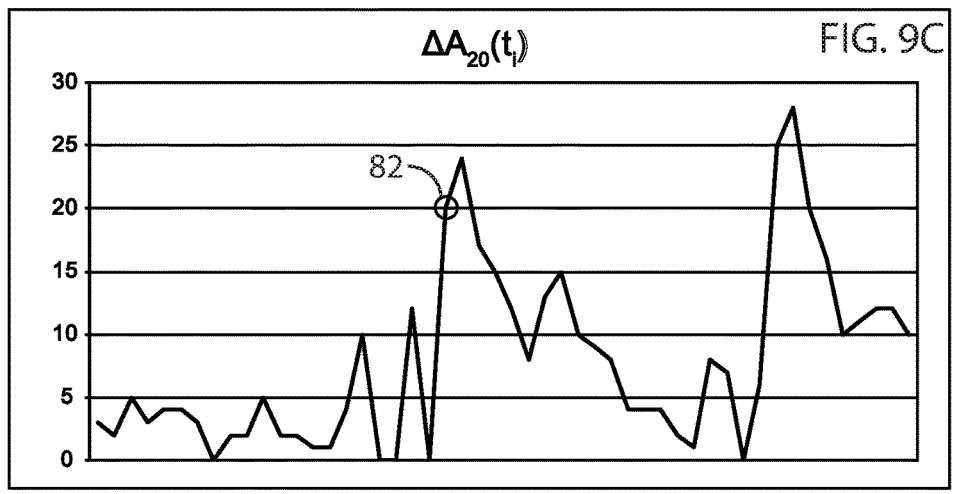

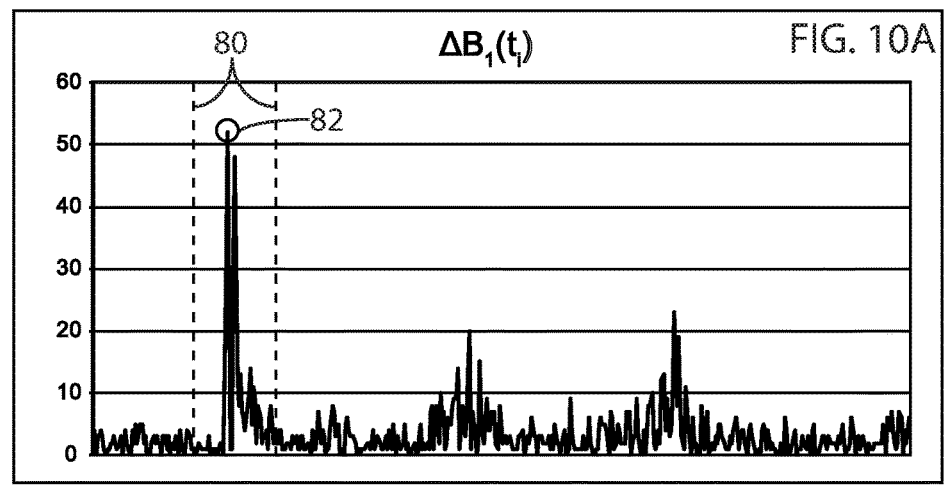
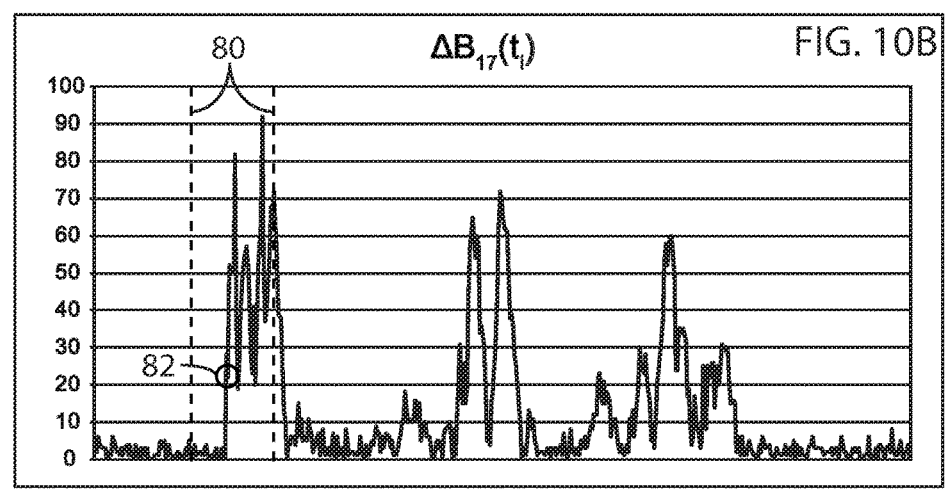
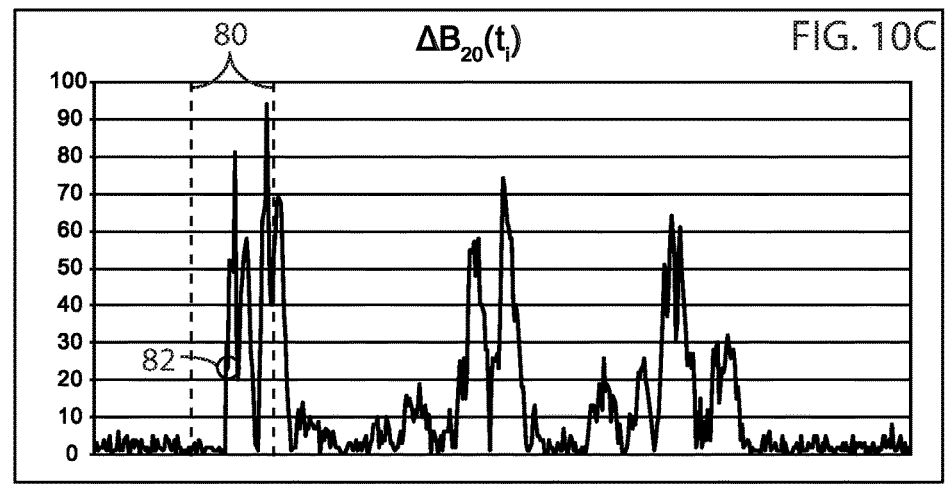

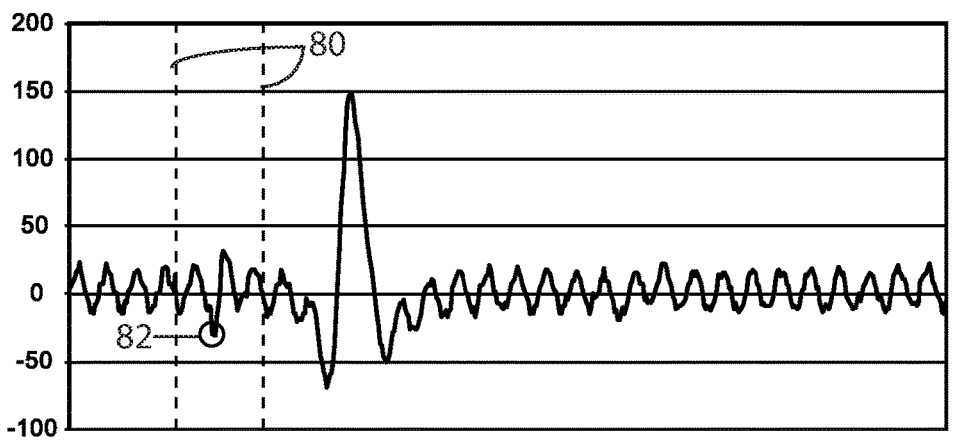
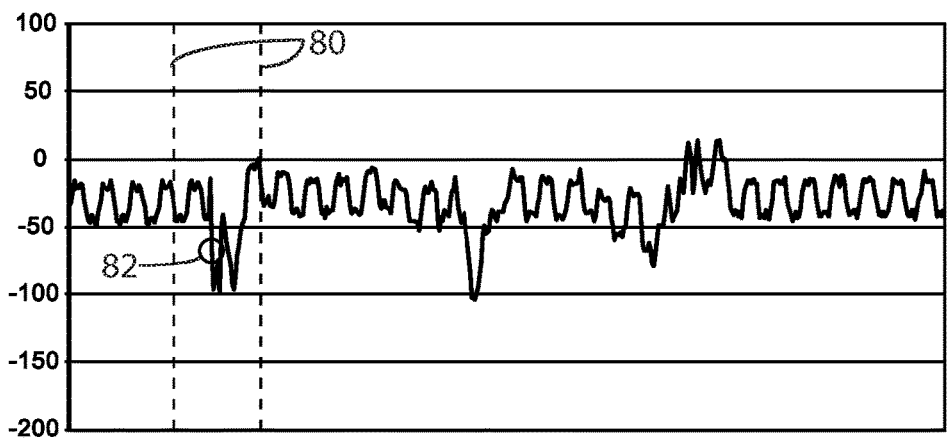

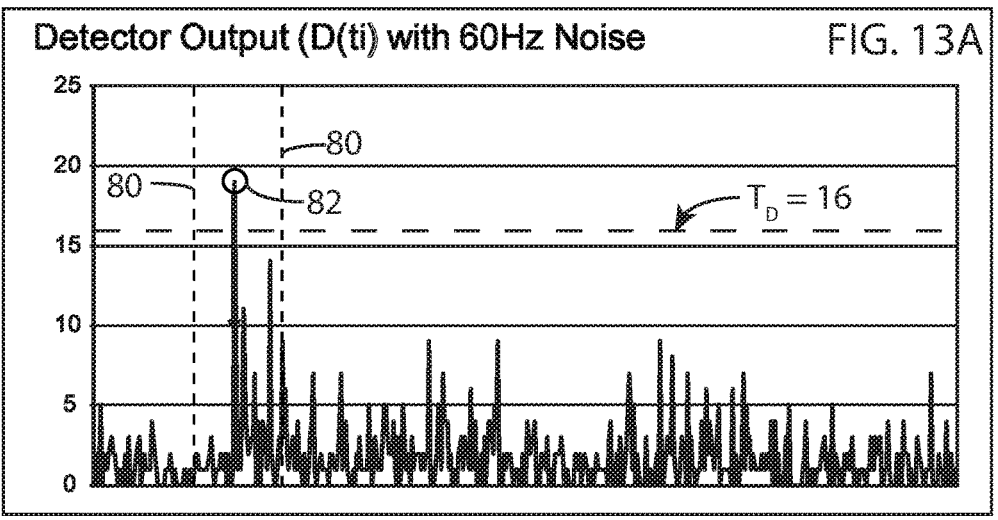
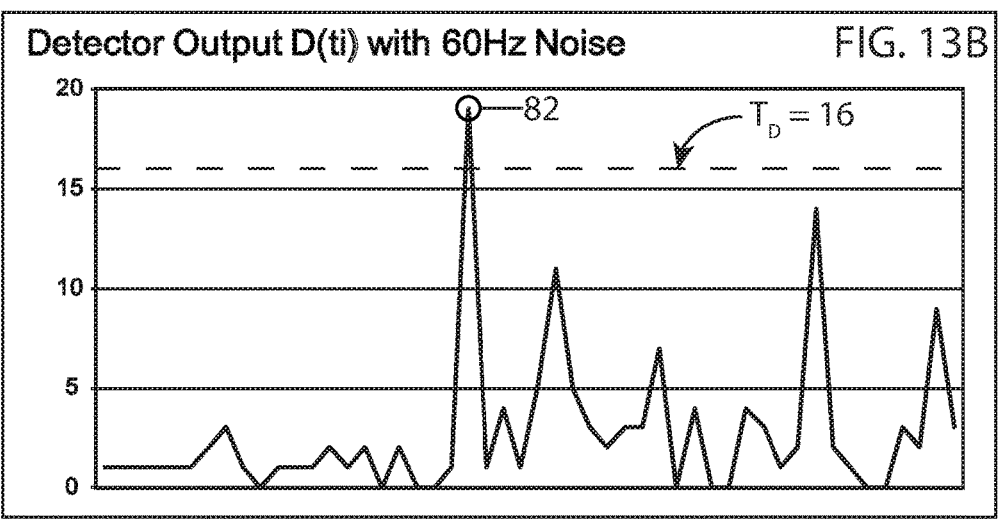

DETECTING STIMULUS PULSES

FIELD OF THE INVENTION

This invention is related generally to the field of electrophysiology, and more particularly to technology for reliable detection of stimulus pulses within electrical signals derived from living bodies.

BACKGROUND OF THE INVENTION

Some subjects, human and animal, require artificial electrical stimulation for the treatment of various symptoms. Patients with heart arrhythmias or heart blocks may utilize implanted pacemakers or combination pacemaker/defibrillators. But also some patients may be artificially stimulated by insertion of catheters into the heart during procedures such as electrophysiological studies. In fact, modern medicine is now exploring many stimulation therapies for hearts, muscles, nerves, and the brain. Some therapies like AV pacing or resynchronization therapy involve the application of multiple electrical pulses in precisely timed patterns to achieve the desired results.

The invention disclosed herein is broadly applicable to the detection of stimulus pulses which are applied to one or more regions (internal or external) of a living body in order to cause muscle or nerve cells to respond in a desired fashion. Cardiac pulses are one example of such stimulus pulses, cardiac pacing pulses such as those produced by cardiac pacemakers. The method of detection of such pulses is described herein in the context of detecting cardiac pacing pulses, but the inventive method is broadly applicable to the detection of many other stimulus pulses having similar signal characteristics. Further, the embodiments of the invention disclosed are also related to cardiac pacing. The use of cardiac pacing for description and illustration is not intended to be limiting.

Interpretation of electrical signals in such situations can often be complicated by the presence of the stimulus artifacts with the physiological signals being studied. In cardiac pacing, effective pacing stimuli normally occur immediately before the heart muscle response, which is generally called a P-wave in the atria or an R-wave in the ventricles. However, pacing stimuli that are sub-threshold, meaning not energetic enough to capture the heart muscle, can occur in isolation with no following muscle electrical response, or at any position within a heart cycle including within any part of the P, QRS and T waves of a naturally-occurring heart cycle. This dyssynchrony of stimulus with response complicates signal interpretation and yet is of critical importance.

In the event that stimulus artifacts (pulses) are mistaken for physiological activity such as heartbeats, devices intended to count heart rate may err. For a bedside cardiac monitor, a worst case occurs when a patient's heart has stopped beating but a heart monitor continues to report a normal heart rate, counting only ineffective pacing artifacts. In such situations, it is possible that no alarm will be given.

Often when a cardiac-paced patient is supervised such as during a procedure or in an ICU, there is less confusion as to when a pacing pulse has occurred. However, during the analysis of recorded signals taking place away from a patient, it may be important to be able to detect pacemaker artifacts in situations in which some confusion may exist in the recorded electrical signals.

The term "pacing spike" is also commonly used to refer to a stimulus artifact or stimulus pulse. The word "spike" is somewhat misleading, however, in that modern cardiac stimuli have become more complicated in shape, having multiple polarities and durations within a single stimulus. Throughout this document, various terms are used when referring to stimulus pulses.

Special electrical circuits operating in the analog domain or the extremely high bandwidth digital domain are usually able to distinguish stimulus artifacts from physiological signals, but these circuits add dramatically to the complexity and cost of equipment and the amount of storage memory required for signals.

Past methods to detect stimulus artifacts are dependent on the difference in signal characteristics of pacing artifacts compared to physiologic signals. Cardiac pacing stimuli tend to be very brief compared to the action potentials of muscle cells which are either naturally occurring or occurring in response to the stimuli. Typical pace pulse stimuli may be about one millisecond (msec) in duration while a QRS complex may be on the order of 100 msec wide.

The dominant pre-existing strategy to rely on the high-frequency content of pace artifacts is reasonable when detection occurs in body surface ECG channels. However, the frequency content of intra-cardiac records, or electrograms (EGM) can be significantly higher, and in appearance certain portions of EGMs are more difficult to distinguish from stimulus artifacts.

Much existing literature relates to implanted devices like pacemakers where the detection of the stimulus is not required because the device itself generates the stimulus. For these devices the interesting issue is how to remove or blank the resulting stimulus artifact so that the implanted device can sense the heart response and determine whether the stimulus was effective or not.

A number of methods for detecting stimulus pulses are known. Among these are methods disclosed in the patent documents described below. U.S. Pat. No. 4,105,023 (Marchese et al.) entitled "Pacemaker Artifact Suppression in Coronary Monitoring" describes a method which uses positive and negative slew rate detectors combined with multiple one-shot timing circuits and coincidence detection circuitry to detect a pace stimulus artifact. The circuitry operates in the analog domain on a single channel body surface ECG signal without digitization.

U.S. Pat. No. 4,149,527 (Naylor et al.) entitled "Pacemaker Artifact Suppression in Coronary Monitoring" discloses a method which uses a rate-limit circuit to detect pace artifacts and selects the rate-limit value (a) to pass those signals having frequency characteristics commensurate with either the normal PQRST complex of an ECG signal or the myoelectric artifacts commonly referred to as muscle noise, and (b) to rate-limit for higher slew rates which are characteristic of the discharge pulse portion of a pacer signal artifact. The Naylor et al. system involves transistor circuitry operating in the analog domain on a single channel ECG signal.

U.S. Pat. No. 4,664,116 (Shaya et al.) "Pace Pulse Identification Apparatus" describes a high-pass filter and comparator circuit with a threshold sensitive to steady high-frequency noise operating in the analog domain on a single ECG channel. The user is warned that some false detections can occur when the electrical equipment causing the high-frequency noise is turned on or its state of operation is changed. When high-frequency noise is present, the circuit reduces its sensitivity to pace artifacts such that small artifacts may not be identified.

U.S. Pat. No. 7,471,977 (Zinser et al.) entitled "Method and System for Detecting Pace Pulses" discloses a system which detects pace pulses in electrocardiogram data by processing one or more sets of electrocardiogram data using a non-linear detection algorithm. The system uses differentiation, negative product accumulation and a cross-multiplicative combiner, requiring significantly more complex calculations than the present invention.

U.S. patent application Ser. No. 14/687,010 (Reinke et al.) entitled "Pace Pulse Detector for an Implantable Medical Device" discloses techniques for detecting pacing pulses in a sensed electrical signal from an implantable medical device (IMD) by analyzing a single sensed electrical signal to detect two types of pulses, one type having a first set of characteristics and the other type having a second set of characteristics. Operation of the IMD is adjusted to account for the detected pulses by, for example, blanking the sensed electrical signal or modifying a tachyarrhythmia detection algorithm. Two other contemporaneously-filed U.S. patent applications (Ser. Nos. 14/686,947 and 14/687,053) include disclosures similar to the '010 application.

In the field of physiology, it is known that physiologic signals conduct as ions crossing cellular membranes and further that the conduction rate of such signals is on the order of 1 meter per second (m/s) in muscle tissue and up to about 120 m/s in nerve tissue. However, stimulus pulses applied to living-body tissue conduct directly as electricity, moving through the body at a rate on the order of 10% of the speed of light. This very high conduction rate compared to the rate of physiologic signals means that stimulus pulses in multi-channel signals occur essentially coincidentally. The present invention exploits this coincidence as a way to discriminate between stimulus pulses and other types of signals in order to find these "needles-in-a-haystack" within captured electrical signals derived from living bodies.

It is therefore desirable to have an efficient, simple and reliable method to automatically recognize the features within electrical signals which indicate the occurrence of an artificial electrical stimulus even when that stimulus occurs coincidental to physiological signals and other noise signals.

OBJECTS OF THE INVENTION

It is an object of this invention, in the field of electrophysiology, to provide an automatic method for accurate and reliable detection of stimulus pulses with a minimum of false positive and false negative detections.

Another object of this invention is to provide a stimulus pulse detection method which advantageously exploits the coincidence of such pulses in a plurality of electrical signals.

Another object of this invention is to provide a stimulus pulse detection method which does not require excessively-high sampling rates as found in some prior art methods.

Another object of this invention is to provide a stimulus pulse detection method which detects a stimulus pulse at the earliest stage within the pulse and preferably during the first sample time period of containing such a pulse.

Another object of this invention is to provide a stimulus pulse detection method which requires only simple arithmetic calculations and thus reduces the computational load of the detection process.

Another object of this invention is to provide a stimulus pulse detection method which operates reliably in the presence of electrical noise such as powerline noise.

Another object of this invention is to provide a stimulus pulse detection method which does not require dedicated analog circuitry.

Another object of this invention is to provide a stimulus pulse detection method which can operate in forward time or backward time.

Another object of this invention is to provide a stimulus pulse detection method which includes automatic selection of the best electrical signals to be employed for detection.

Yet another object of this invention is to provide a stimulus pulse detection method which allows post-detection operations such as blanking.

These and other objects of the invention will be apparent from the following descriptions and from the drawings.

SUMMARY OF THE INVENTION

The invention is a method for detecting a stimulus pulse by using two or more electrical signals derived from a living body. The method comprises the following steps: (a) for each electrical signal, digitizing the signal with an analog-to-digital converter to produce a sampled signal $S_k$; (b) for each signal $S_k$ at a sample time $t_i$, computing a primary difference $\Delta_{kp}(t_i) = \text{abs}[S_k(t_i) - S_k(t_{i-p})]$; (c) determining the minimum value of all of the computed differences, such minimum being a detector output $D(t_i)$; (d) comparing the detector output $D(t_i)$ with a detection threshold; and (e) indicating that a stimulus pulse has been detected when the detector output $D(t_i)$ is above the detection threshold. In some preferred embodiments, the value of the variable p is equal to 1, and in other embodiments, the value of the variable p is equal to −1.

Some preferred embodiments of the inventive method for stimulus pulse detection method further include the step of determining the detection threshold based on the maximum value $D_{max}$ of detector output $D(t_i)$ over a time period $t_{th1}$, and in some of these embodiments, the detection threshold is a constant times $D_{max}$.

One highly-preferred embodiment of the inventive method further includes the steps of determining the maximum value $DNS_{max}$ of non-stimulus-pulse local peaks of detector output $D(t_i)$ in a period of time $t_{th2}$ before a detected stimulus pulse and a period of time $t_{th3}$ after a detected stimulus pulse, determining hardware-only noise $D_{inst}$ in the detector output $D(t_i)$, and computing the detection threshold as a first constant times the sum of $DNS_{max}$ and $D_{inst}$ plus a second constant times $D_{max}$.

Other preferred embodiments further include the step of determining the detection threshold based on the maximum value $DNS_{max}$ of non-stimulus-pulse local peaks of detector output $D(t_i)$ in a period of time $t_{th3}$ after a detected stimulus pulse and the detection threshold is a constant plus $DNS_{max}$.

Some embodiments of the stimulus pulse detection method of this invention further include the step of suppressing indication of additional stimulus pulse detections for a period of time $t_S$ after a stimulus pulse is detected. Other embodiments of the inventive method further include the step of removing a detected stimulus pulse from one or more of the signals.

Some additional preferred embodiments of the inventive method include the step of automatically selecting the two or more electrical signals from a set of electrical signals derived from a living body. Some of these embodiments include determining a figure-of-merit of combinations of electrical signals from the set of electrical signals.

In highly-preferred embodiments, the inventive stimulus pulse detection method further includes for each sampled signal $S_k$ at sample time $t_i$, computing one or more other differences $\Delta_{kf}(t_i) = \text{abs}[S_k(t_i) - S_k(t_{i-f})]$, each other difference using a unique value for f. Such other differences are computed prior to determining the minimum value of all of the computed differences. In some of these highly-preferred embodiments, the variable p is equal to 1 and all values of f are positive. In some such embodiments, at least one of the values of f is a non-integer value and the values of $S_k(t_{i-f})$ are determined by interpolation using neighboring values of the corresponding sampled signal $S_k$. In other highly-preferred embodiments, all values of f are positive integers.

In other embodiments, the variable p is equal to −1 and all values of f are negative. In some of these embodiments, at least one of the values of f is a non-integer value and the values of $S_k(t_{i-f})$ are determined by interpolation using neighboring values of the corresponding sampled signal $S_k$. In other embodiments, all values of f are negative integers.

In some highly-preferred embodiments of the inventive stimulus pulse detection method, at least one f value is chosen to filter out noise at a frequency selected from the group consisting of 50 Hz, 60 Hz and 400 Hz.

In other highly-preferred embodiments, the digitizing of the two or more electrical signals is done at a sampling rate which is evenly divisible by each of the one or more values of f.

The invention is a method which is conveniently illustrated using block diagrams or flow charts to describe the various steps of the inventive method and the embodiments thereof. As used herein, the terms such as "step", "flow chart element", "process element" or other similar terms may be used to describe the various individual parts of the block diagrams or flow charts. Used as such, there is no intended difference in the meaning of these terms. When an embodiment is illustrated in more than one figure, the term "process portion" and "process" are used herein interchangeably. Specific reference numbering makes such interchangeable usage unambiguous.

The term "sampled signal" as used herein refers to a stream of digital numeric values at discrete points in time. For example, an analog signal of an electrical voltage is digitized every millisecond (msec) using an analog-to-digital (A/D) converter to generate a series of sequential digital numeric values one millisecond apart. The examples presented herein use this sampling rate of 1,000 sps, producing streams of digital values one millisecond apart. This sampling rate is not intended to be limiting; other sampling rates may be used.

The mathematical expressions and statements used in the claims are well-known to those skilled in the art of mathematics and signal processing. However, to avoid any possible confusion, as used herein, the notation $S_k$ represents a sampled signal, and since there are two or more such sampled signals, k=1 to n where n≥2. At each sample time $t_i$, each of the n sampled signals has a digital value at such time represented by the notation $S_k(t_i)$. The time index i consists of integer values as is well-known in the art.

The notation $\Delta_{kp}(t_i)$ represents the primary difference which is the absolute value of the difference between the quantity $S_k(t_i)$ and $S_k(t_{i-p})$. There are n such primary differences at each sample time $t_i$.

The notation $\Delta_{kf}(t_i)$ represents another difference which is the absolute value of the difference between the quantity $S_k(t_i)$ and $S_k(t_{i-f})$. There may be m values for the variable f, and thus there may be n times m (n×m) such other differences (m differences at each value of k) at each sample time $t_i$. Thus, the number of differences over which the minimum value is determined is (m+1)×n. The variable m may be as small as 0, and therefore the smallest number of differences over which the minimum value is determined is n.

The notation $D(t_i)$ represents the output of the detection filter at sample time $t_i$. $D(t_i)$ is determined prior to any comparison with a detection threshold $T_D$. During operation of the inventive stimulus pulse detection method described herein, detector output $D(t_i)$ is computed at each sample time $t_i$. Thus, the notation $D(t_i)$ may refer to a value of detector output at a specific sample time $t_i$ as well as the stream of computed values of the detector output. The context of such usages are clear from the context in which they are found.

BRIEF DESCRIPTION OF THE DRAWINGS

FIG. 3 is a partial schematic block diagram of a modification to the method embodiments of FIGS. 1-2B in which indication of a stimulus pulse detection is suppressed for a period of time after a previous stimulus pulse has been detected.

FIG. 3A is a partial schematic block diagram of a modification to the method embodiments of FIGS. 1-2B in which a stimulus pulse is removed from one or more of the signals for a period of time $t_R$.

FIGS. 5A and 5B are time-plots of portions of exemplary cardiac electrical signals derived from a human patient. The time span of the plots of FIGS. 5A and 5B are the same.

FIGS. 6A and 6B are expanded portions of the time-plots of FIGS. 5A and 5B, respectively. The time spans of FIGS. 6A and 6B are indicated in FIGS. 5A and 5B with vertical dotted lines.

FIGS. 8A-8C are time-plots of exemplary difference terms computed from the signals of FIG. 5A as elements in the inventive stimulus pulse detection method. The time spans of these plots are identical to those of FIGS. 5A and 5B.

FIGS. 9A-9C are expanded time-plots of portions of the plots of FIGS. 8A-8C, respectively. The time spans of these plots are indicated on FIGS. 8A-8C with vertical dotted lines.

FIGS. 10A-10C are time-plots of exemplary difference terms computed from the signals of FIG. 5B as elements in the inventive stimulus pulse detection method. The time spans of these plots are identical to those of FIGS. 5A and 5B.

FIGS. 12A and 12B are time-plots of portions of exemplary cardiac electrical signals, derived from a human patient, to which 60 Hz noise has been added to illustrate the performance of the inventive stimulus pulse detection method in the presence of significant powerline noise. The time span of the plots of FIGS. 12A and 12B are identical to those of FIGS. 5A and 5B.

FIG. 13A is a time-plot of the detector output of an exemplary embodiment of the inventive method, computed from the electrical signals of FIGS. 12A and 12B. The time span of FIG. 13A is identical to that of FIGS. 12A and 12B.

FIG. 13B is an expanded portion of the time-plot of FIG. 13A. The time span of FIG. 13B is indicated on FIG. 13A and is identical to the indicated time spans in FIGS. 12A and 12B.

DETAILED DESCRIPTION OF PREFERRED EMBODIMENTS

Figure 1:
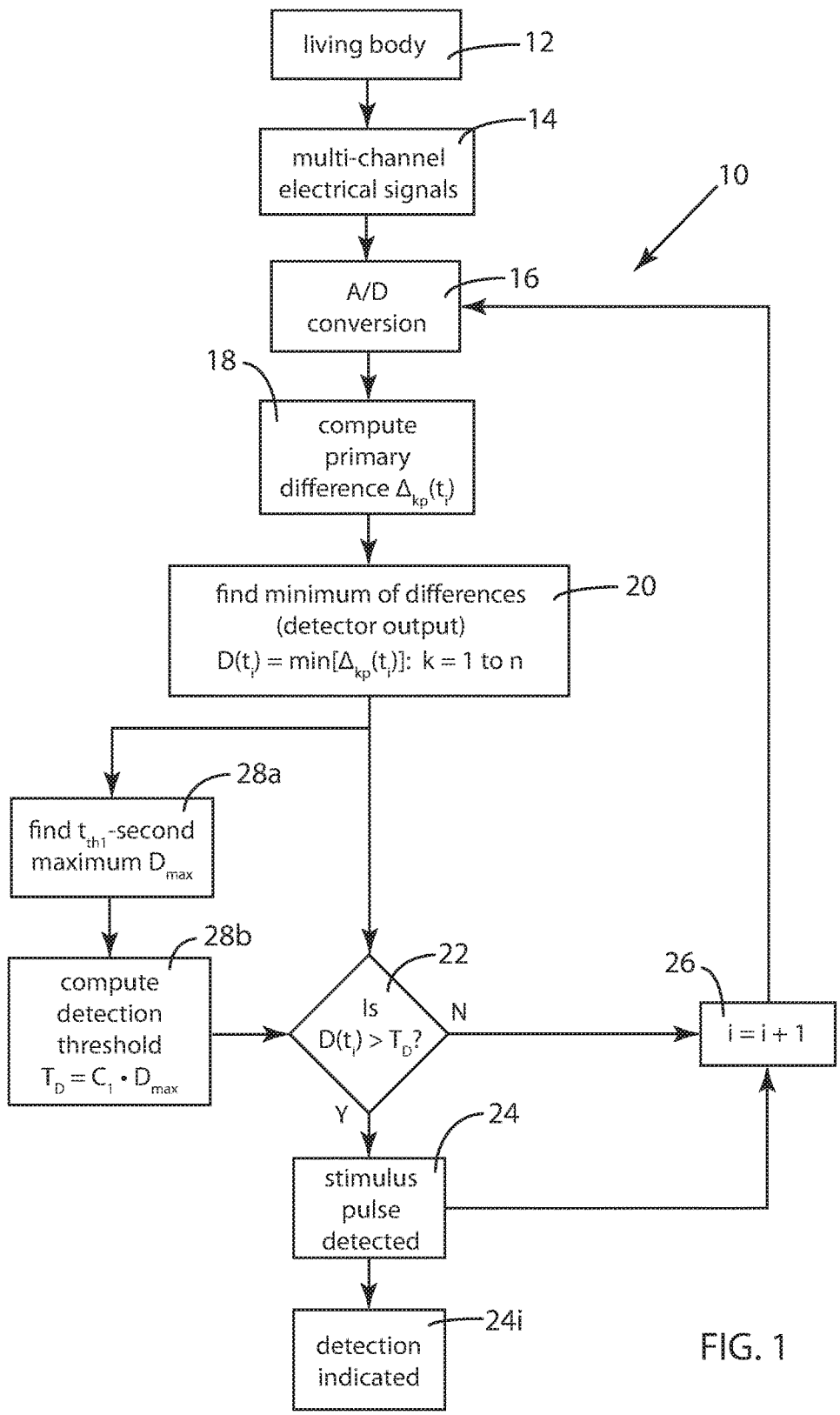
FIG. 1 is a schematic block diagram of one embodiment of the inventive method for detecting a stimulus pulse using two or more electrical signals from a living body. This embodiment includes computing primary differences for each of the electrical signals, and the detection threshold is determined based on the maximum detection filter value over a period of time.
Figure 2:
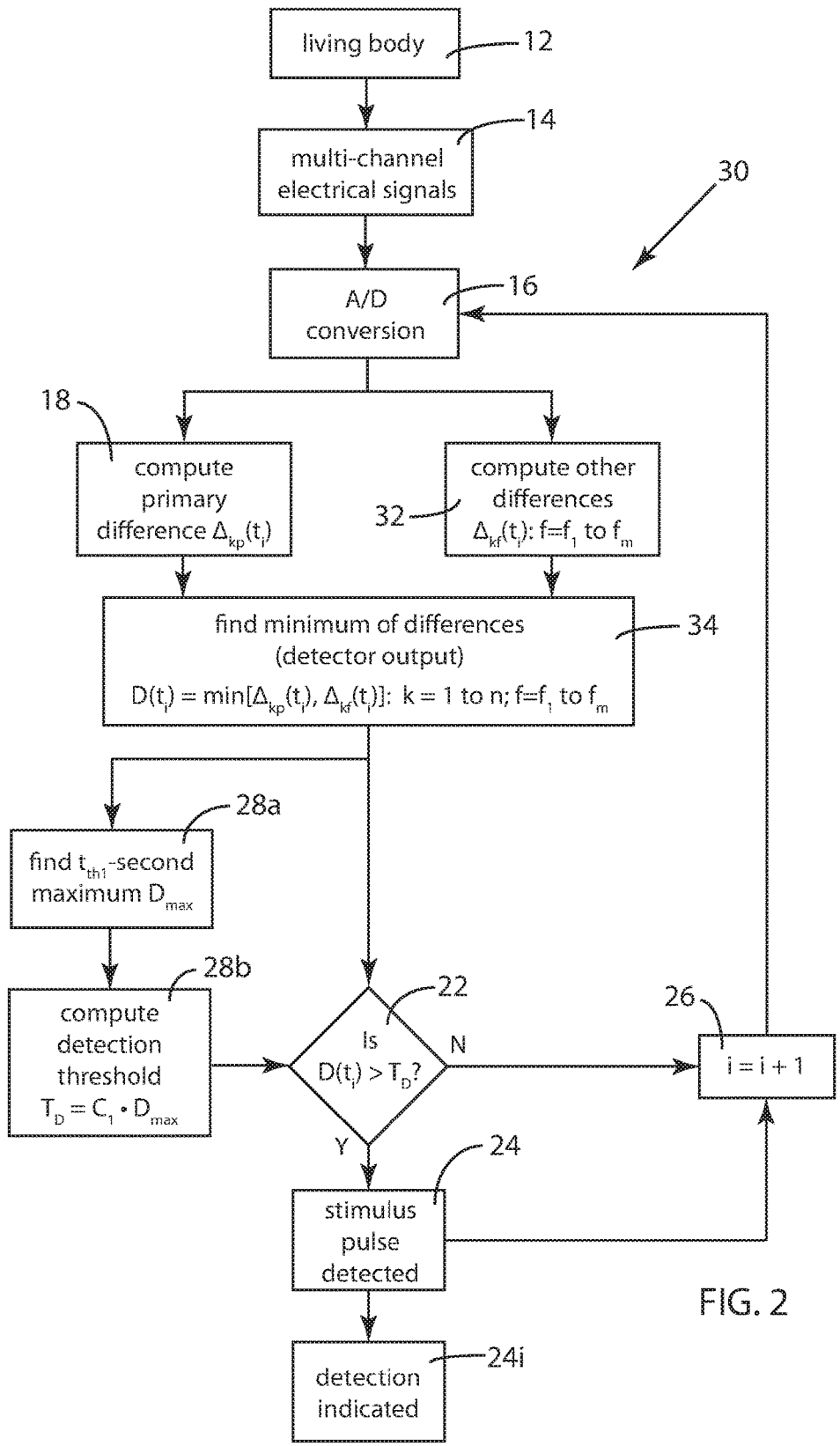
FIG. 2 is a schematic block diagram of an alternative embodiment of the inventive method for detecting a stimulus pulse using two or more electrical signals from a living body. This embodiment includes computing primary differences and one or more other differences for each of the electrical signals, and the detection threshold is determined based on the maximum detection filter value over a period of time.

Each of FIGS. 1-4 is a schematic block diagram illustrating an embodiment of the inventive method for stimulus pulse detection or of portions of such embodiments. Each block diagram elements (process portion or flow chart component) represents a step or element in the method which will be described in detail below. FIGS. 1-2B each illustrate different embodiments of the inventive method. FIG. 1 is a block diagram of an embodiment 10 of the inventive method. A living body 12 is the source of multi-channel set 14 of electrical signals. As mentioned above, multi-channel signals 14 may be any number of types of signals derived from living body 12. Multi-channel signals 14 may come from electrodes such as body-surface ECG and intracardiac electrodes, either obtained by implanted devices or by invasive wires or catheters. In addition, other living-body sources such as but not limited to brain wave signals from EEG systems may be the source of stimulus pulses. By way of example, the embodiments described herein will generally be described as cardiac signals in which a pacing pulse (pacing spike) is the particular stimulus pulse being detected. More specifically, the illustrative numerical examples of the operation of the inventive method used herein involve the detection of pacing spikes in multi-channel cardiac signals.

Referring again to FIG. 1, each signal in multi-channel electrical signals 14 is converted to a sequential stream of digital values by an analog-to-digital converter 16, one such digital value at each sampling time $t_i$. A common sampling rate is on the order of 1,000 samples per second (sps), and the examples presented later in this document use a sampling rate of 1,000 sps. Many other sampling rates are possible. However, one of the advantages of the inventive method described herein is that the method enables the use of such a relatively slow (and therefore much more affordable) sampling rate.

Implicit in each figure illustrating the steps of the inventive method is the use of computer-based apparatus which enables the automated steps of the inventive method to be carried out much more rapidly than would be possible without such processing apparatus. Most of the method steps require action carried out at each sampling time $t_i$ in order to be effective as a stimulus pulse detector.

An example of such computation occurs in a process element 18 in which for each signal in digitized multi-channel electrical signals 14 which is being processed in method embodiment 10, a primary difference $\Delta_{kp}$ is computed at each sample time $t_i$. The notation $\Delta_{kp}(t_i)$ represents the $k^{th}$ primary difference computed as $\Delta_{kp}(t_i)=abs[S_k(t_i)-S_k(t_{i-p})]$, where $S_k(t_i)$ is the digital value of the $k^{th}$ electrical signal at sample time $t_i$ and p is the number of sample times away from time $t_i$ of the digital value of $S_{kp}(t_{i-p})$. For example, if p=1, then $\Delta_{kp}(t_i)=abs[S_k(t_i)-S_k(t_{i-1})]$, i.e., the primary difference is the absolute value of the difference between the digital value $S_k$ and its immediately preceding sampled value. For a sampling rate of 1,000 sps, the values of $S_k$ are therefore 1 millisecond (msec) apart. If the number of electrical signals being used in the inventive method is two (n=2), then there are two primary differences $\Delta_{1p}(t_i)$ and $\Delta_{2p}(t_i)$ at each sample time. Also as an example, if p=−1, then $\Delta_{kp}(t_i)=abs[S_k(t_i)-S_k(t_{i+1})]$, i.e., the primary difference is the absolute value of the difference between the digital value $S_k$ and its immediately following sampled value. Such analysis within the inventive method therefore encompasses backward time analysis to deal with signals over which the detector is detecting stimulus pulses in, for example, already recorded signals. The inventive method is equally valid for forward or backward time applications.

Method embodiment 10 employs a plurality of primary differences only. The next step (process step 20) in method embodiment 10 is to find, at each sample time $t_i$, the minimum value of the differences $\Delta_{kp}(t_i)$ computed in method step 18, and such minimum-of-differences is the value of a detector output $D(t_i)$. In our n=2 example, at each sample time $t_i$, the smaller of the two values $\Delta_{1p}(t_i)$ and $\Delta_{2p}(t_i)$ becomes $D(t_i)$.

In method step 22, detector output signal $D(t_i)$ is compared to a detection threshold $T_D$, and if $D(t_i)$ is not greater than $T_D$, then method embodiment 10 proceeds to the next sample time $t_{i+1}$, and operation of stimulus pulse detection method 10 continues as explained above using the next sampled values of multi-channel signals 14. However, if $D(t_i)$ is greater than $T_D$, then method embodiment 10 proceeds to method step 24 which represents the detection of a stimulus pulse at sample time $t_i$. Method embodiment 10 then proceeds to method step 24i in which the detection of step 24 is indicated in some fashion within the system employing embodiment 10.

Figure 1A:
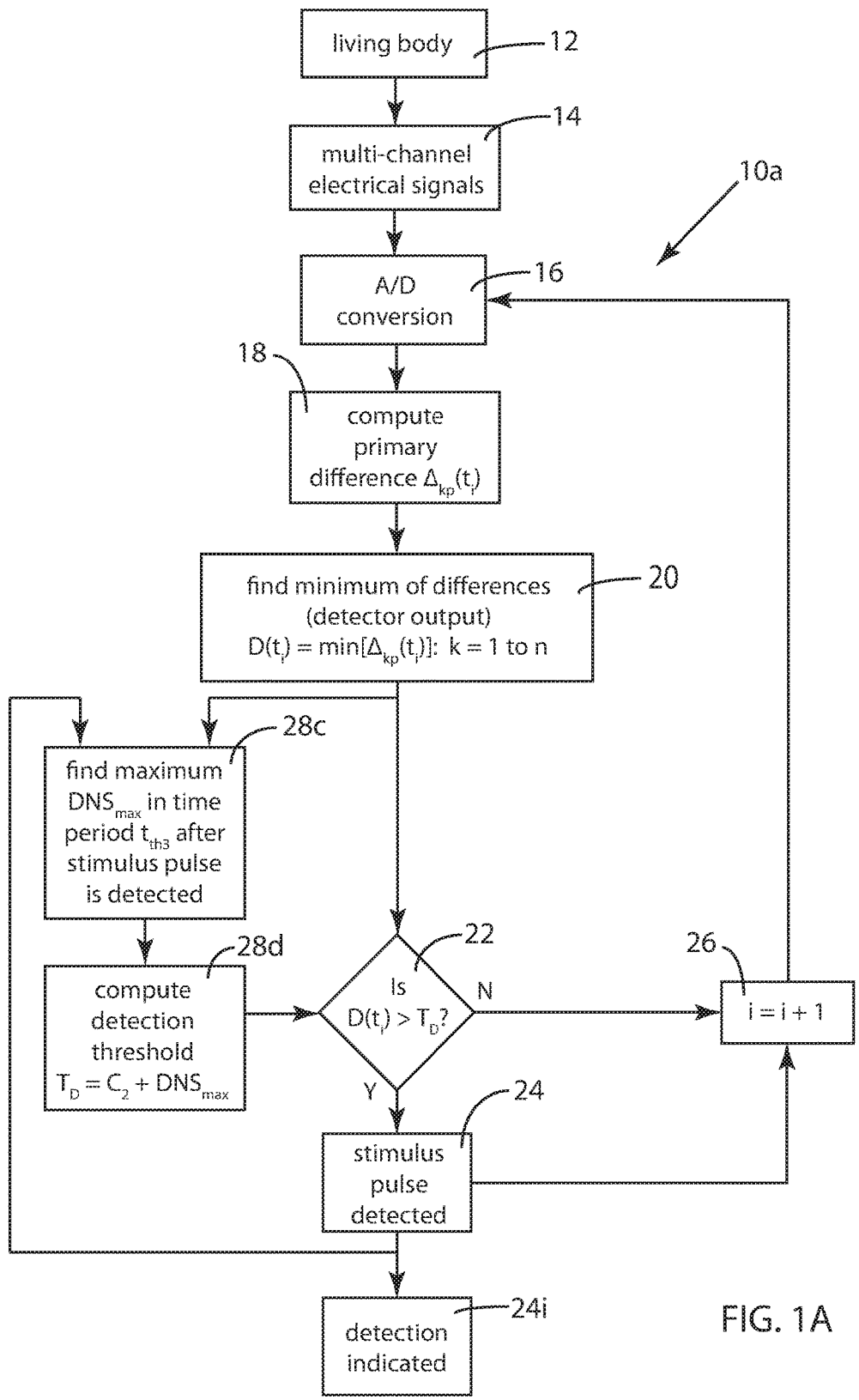
FIG. 1A is a schematic block diagram of the embodiment of FIG. 1 but including an alternative method for determining the value of the detection threshold in which the detection threshold is based on the maximum of non-stimulus-pulse local peaks of the detection filter value during a time period after a stimulus pulse is detected.
Figure 1B:
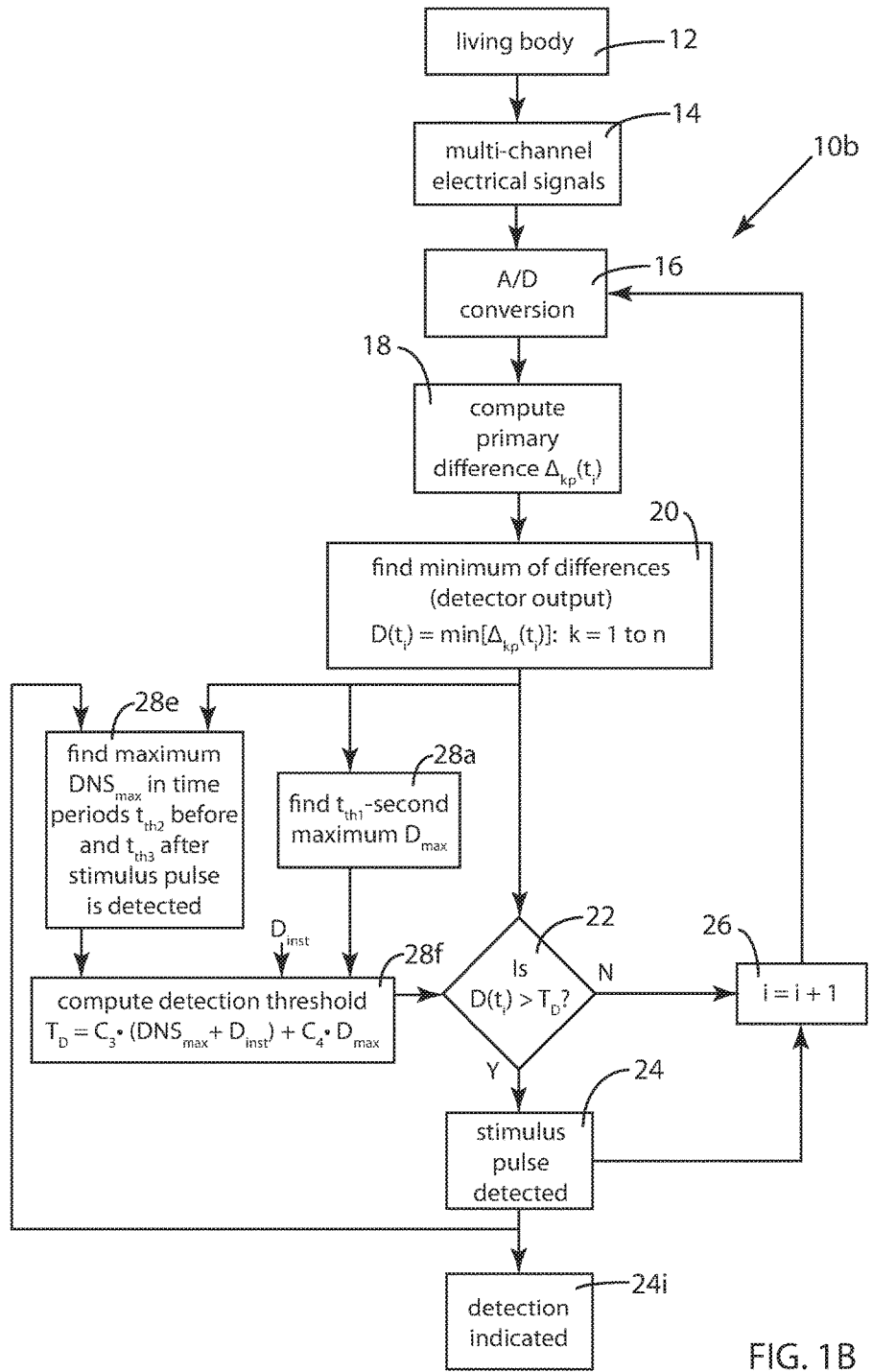
FIG. 1B is a schematic block diagram of the embodiment of FIG. 1 but including a second alternative method for determining the value of the detection threshold. This second alternative involves determining a maximum of non-stimulus local peaks during time periods both before and after a stimulus pulse is detected.

The embodiments illustrated in FIGS. 1, 1A and 1B each has the method steps which have been described above for method embodiment 10. Embodiment 10A of FIG. 1A and embodiment 10B of FIG. 1B differ from embodiment 10 in the process steps employed to compute the value of detection threshold $T_D$. In method step 28a of embodiment 10, the maximum value $D_{max}$ of detector output $D(t_i)$ is determined over a period of time $t_{th1}$, and in method step 28b this maximum $D_{max}$ is multiplied by a constant $C_1$ to determine $T_D$. For example, $t_{th1}$ may have a value of 2 seconds, and the value of detection threshold $T_D$ may be updated accordingly every 2 seconds. The value of the constant $C_1$ is set such that stimulus pulses are detected with a minimum of false positive and false negative detections. That is, the value of $C_1$ in embodiment 10 should be such that the relatively high values of the stimulus pulses are above detection threshold $T_D$ while signal noise and non-stimulus-pulse peaks in the physiological signals should fall below threshold $T_D$. Values on the order of 0.25 to 0.5 have been found to be useful, but such a value is not intended to be limiting.

Method step 28a may be realized by at least two approaches to such updating. For example, time period $t_{th1}$ may be applied such that threshold $T_D$ is updated only after a completely new $t_{th1}$-second period has been processed to find the maximum $D_{max}$. Alternatively, time period $t_{th1}$ may be applied as a moving window such that at every sample time $t_i$, the maximum $D_{max}$ is determined using the immediately-past time period $t_{th1}$. Thus, the value of detection threshold $T_D$ may be updated often under such an approach. Other variations to the way in which the maximum value $D_{max}$ is determined in method step 28a are envisioned within the scope of this invention; the two approaches described here are not intended to be limiting.

FIG. 1A is a schematic block diagram of an embodiment 10a which differs from embodiment 10 only in the method steps used to determine detection threshold $T_D$. In method step 28c of embodiment 10a, a non-stimulus pulse maximum value $DNS_{max}$ of detector output $D(t_i)$ is determined over a period of time $t_{th3}$ after a stimulus pulse, and in method step 28d a constant $C_2$ is added to this maximum $DNS_{max}$ to determine $T_D$. $DNS_{max}$ may be considered to represent noise independent of stimulus pulse levels and is based on local subsidiary peaks (non-stimulus pulses) in the $D(t_i)$ signal from method step 20.

In a fashion similar to FIG. 1A, FIG. 1B is a schematic block diagram of an embodiment 10b which differs from embodiments 10 and 10a only in the method steps used to determine detection threshold $T_D$. In method embodiment 10b, both $D_{max}$ (from method step 28a) and $DNS_{max}$ (from a method step 28e) are used in a method step 28f to determine a value for detection threshold $T_D$. In method step 8e and differing from method step 28c, $DNS_{max}$ is found over a time period $t_{th2}$ before a stimulus pulse occurred as well as a time period $t_{th3}$ after the stimulus pulse occurred. In addition, a noise term $D_{inst}$ is used in the determination of detection threshold $T_D$. $D_{inst}$ represents the noise of the instrumentation involved in capturing the electrical signals and is not related to any physiological signal source. In embodiment 10b, detection threshold $T_D$ is the sum of two terms, one term consisting of the sum of the local subsidiary peak maximum $DNS_{max}$ and the small fixed signal floor $D_{inst}$, and the other term consisting of the difference between $D_{max}$ and this first term. The two terms are weighted by a ratio constant $C_4$. This relationship is as follows:

$$T_D = (DNS_{max} + D_{inst}) + C_4 \cdot [D_{max} - (DNS_{max} + D_{inst})]$$

and can be algebraically reduced to:

$$T_D = C_3 \cdot (DNS_{max} + D_{inst}) + C_4 \cdot D_{max}$$

where the constant $C_3 = 1 - C_4$. As above, constant $C_4$ may have values of between 0.25 to 0.5, but such a range is not intended to be limiting.

The time periods $t_{th2}$ and $t_{th3}$ may each have the same or different values, and the detection threshold $T_D$ may be updated accordingly every time a detection occurs. The length of time periods $t_{th2}$ and $t_{th3}$ may be chosen to ensure that within such time periods no stimulus pulses occur and that the detector output signals $D(t_i)$ during such periods are representative of the high local non-stimulus-pulse maxima in $D(t_i)$. It is also anticipated that one of these time periods may also have a duration of zero. For example, $t_{th2}$ may be zero, and the value of $DNS_{max}$ may be determined only from local peaks occurring for a time period $t_{th3}$ after a stimulus pulse is detected.

Time periods $t_{th2}$ and $t_{th3}$ (also herein called inspection windows) provide control over maximizing the region of detector output signal $D(t_i)$ that is inspected for high levels of filter output which may be due to signal components other than the stimulus pulses. A good value detection threshold $T_D$ will be slightly higher than the highest level of $D(t_i)$ in which no stimulus pulses are present.

For example, in the field of cardiology, there are many scenarios in which the kind of stimulus pulses ("pacing pulses") that may be present is either known or quickly evident after a cardiologist is able to observe some of the electrical cardiac signals (body surface and/or intracardiac signals) available from a patient. In the sections below, four scenarios are described to illustrate the utility of having signal inspection time windows before ($t_{th2}$) and after ($t_{th3}$) each detected stimulus pulse which are independent of each other.

Scenario 1: Single-chamber Constant-rate Pacing

In this scenario, the time intervals between stimulus pulses are constant and normally longer than in other scenarios since each individual pacing pulse will usually be causing a single heartbeat at a sustainable heart-rate interval for the patient's survival, e.g., 300 msec to 1,000 msec in humans. For example, a technician may set $t_{th2} = t_{th3} = 580$ msec—for heart rates less than 100 beats per minute (bpm). The inspection windows $t_{th2}$ and $t_{th3}$ in this example are 20 msec less than the actual intervals (600 msec or more) to neighboring pacing pulses to allow for the non-zero width of each actual pacing pulse.

Scenario 2: Atrio-ventricular (AV) Pacing

In this scenario, a stimulus pulse may be given to an atrium and a second pulse to a different site, usually a ventricle. This is normally done because of a defect in the normal conduction system of a heart which would otherwise automatically stimulate the ventricle from the activity in the atrium. In such a situation, the subject has one heartbeat for every two stimulus pulses, and these pulses occur in more closely coupled pairs. For example, the ventricular stimulus pulses may occur 140 msec after the atrial stimulus pulse. The next atrial stimulus pulse may occur 717 msec after the preceding ventricular stimulus. Such an AV pacing scheme allows the ventricle 140 milliseconds to fill with blood during atrial contraction and provides a heart rate of 70 bpm (total interval is 857 msec). If the stimulus detection logic keeps track of the pattern of already-detected stimulus pulses and has the foreknowledge of AV pacing, when a stimulus pulse is detected and believed to be an atrial stimulus, values for the inspection windows of $t_{th2}$=697 msec and $t_{th3}$=120 msec will survey all the neighboring signals where no additional stimulus pulse exist. (These values are each 20 msec smaller to compensate for the width of the stimulus pulses.) Alternately, the next detected stimulus pulse, if believed to be the ventricular stimulus, may swap the settings to $t_{th2}$=120 msec and $t_{th3}$=697 msec.

Scenario 3: Cardiac Resynchronization Therapy
(Bi-ventricular Pacing)

In this scenario, two stimulus pulses are given, one to each ventricle. These stimuli are physically distinct but are either generally close in time or simultaneous. The purpose of cardiac resynchronization therapy is to cause both ventricles to contract together in order, for example, to maximize cardiac output. The two chambers of the heart share a wall between them called the septum, and maximum efficiency occurs when both chambers contract at the same time that the septum contracts. If the two stimulus pulses are truly simultaneous, then for purposes of detection within the cardiac electrical signals, the two stimulus pulses may be treated as a single stimulus pulse, and the $t_{th2}$ and $t_{th3}$ inspection windows may both be set to slightly less than the expected heart-rate interval. However, if the interval between the two stimulus pulses is non-zero but short, one and then the other of $t_{th2}$ and $t_{th3}$ should be set to either zero or less than the delay, in an alternating fashion as in the AV pacing scenario.

Scenario 4: Induction Pacing or Overdrive Pacing
(Pacing Trains)

These are pacing strategies which employ multiple pacing pulses, usually delivered to a single location in the heart but in a sequence of changing intervals. This is generally only done in an electrophysiology lab (EP lab) and usually requires a dedicated stimulus pulse generating instrument to provide the programmable stimulus pattern. A pacing train of stimulus pulses consists of a set of stimulus pulses which has a first stimulus-pulse interval followed by a second, usually shorter stimulus-pulse interval. Because the pattern of the stimulus pulse train is known to the EP doctor, the stimulus pulse detection method of this invention may also be informed of the pattern, and $t_{th2}$ and $t_{th3}$ inspection windows may be appropriately adapted as the method identifies each stimulus in the sequence.

To summarize, the values of $t_{th2}$ and $t_{th3}$ may be independently set within a wide range of values, say from 0 to 1,000 msec depending on the application of the stimulus pulse detector. The essential concept is that these values be determined such that during these inspection time windows, no stimulus pulses occur which cause detection threshold $T_D$ to be incorrect.

FIG. 2 is a schematic block diagram of an alternative embodiment 30 of the inventive method for detecting a stimulus pulse using two or more electrical signals from a living body. Method embodiment 30 is similar to method embodiment 10 shown in FIG. 1 except that an additional set of other differences $\Delta_{kf}(t_i)$ for f=$f_1$ to $f_m$ are computed in a method step 32, and method step 20 is replaced with method step 34 since the number of differences over which the minimum is found is larger than in method embodiment 10.

Figure 2A:
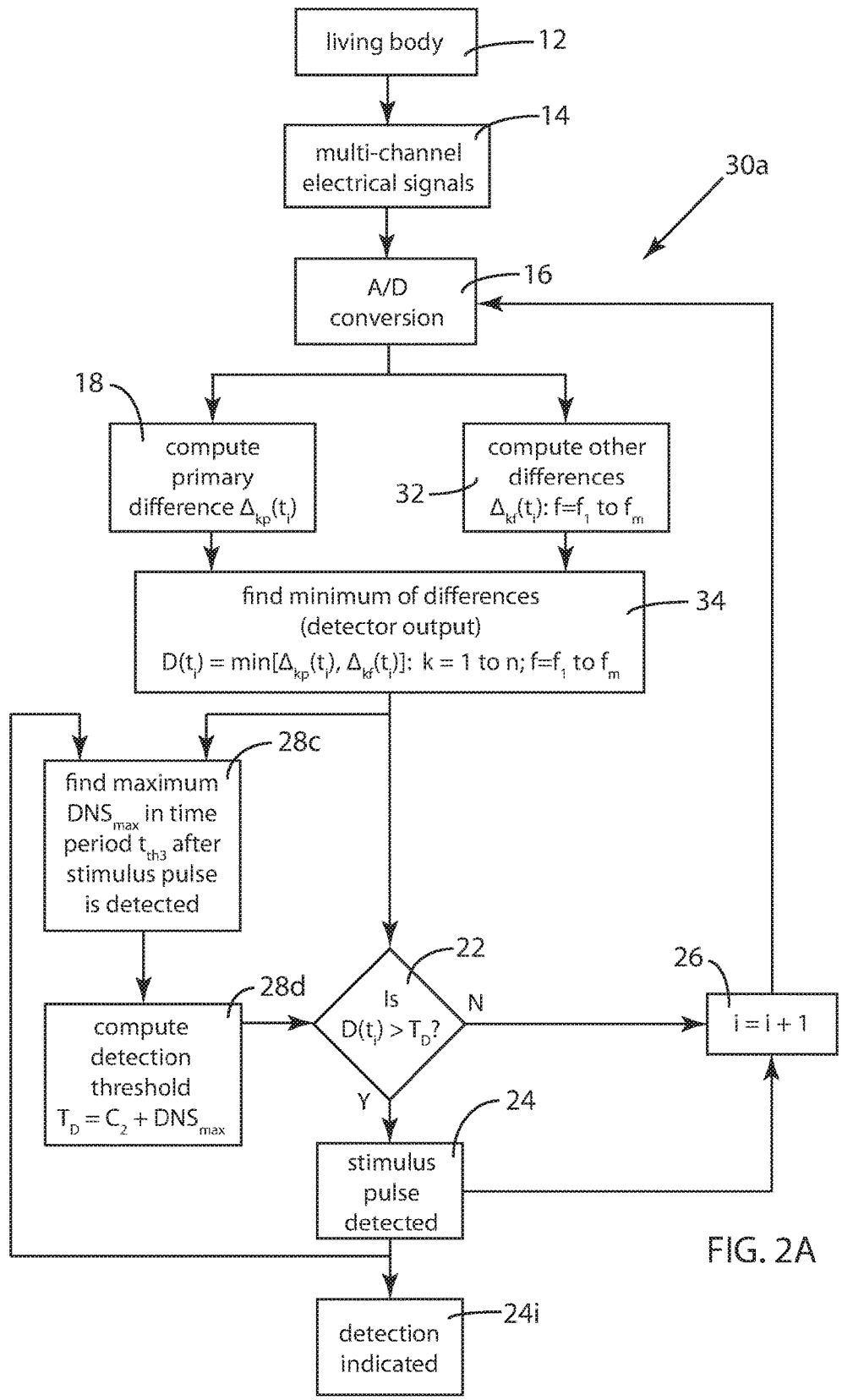
FIG. 2A is a schematic block diagram of the alternative embodiment of FIG. 2 but including an alternative method for determining the value of the detection threshold in which the detection threshold is based on the maximum of non-stimulus-pulse local peaks of the detection filter value during a time period after a stimulus pulse is detected.
Figure 2B:
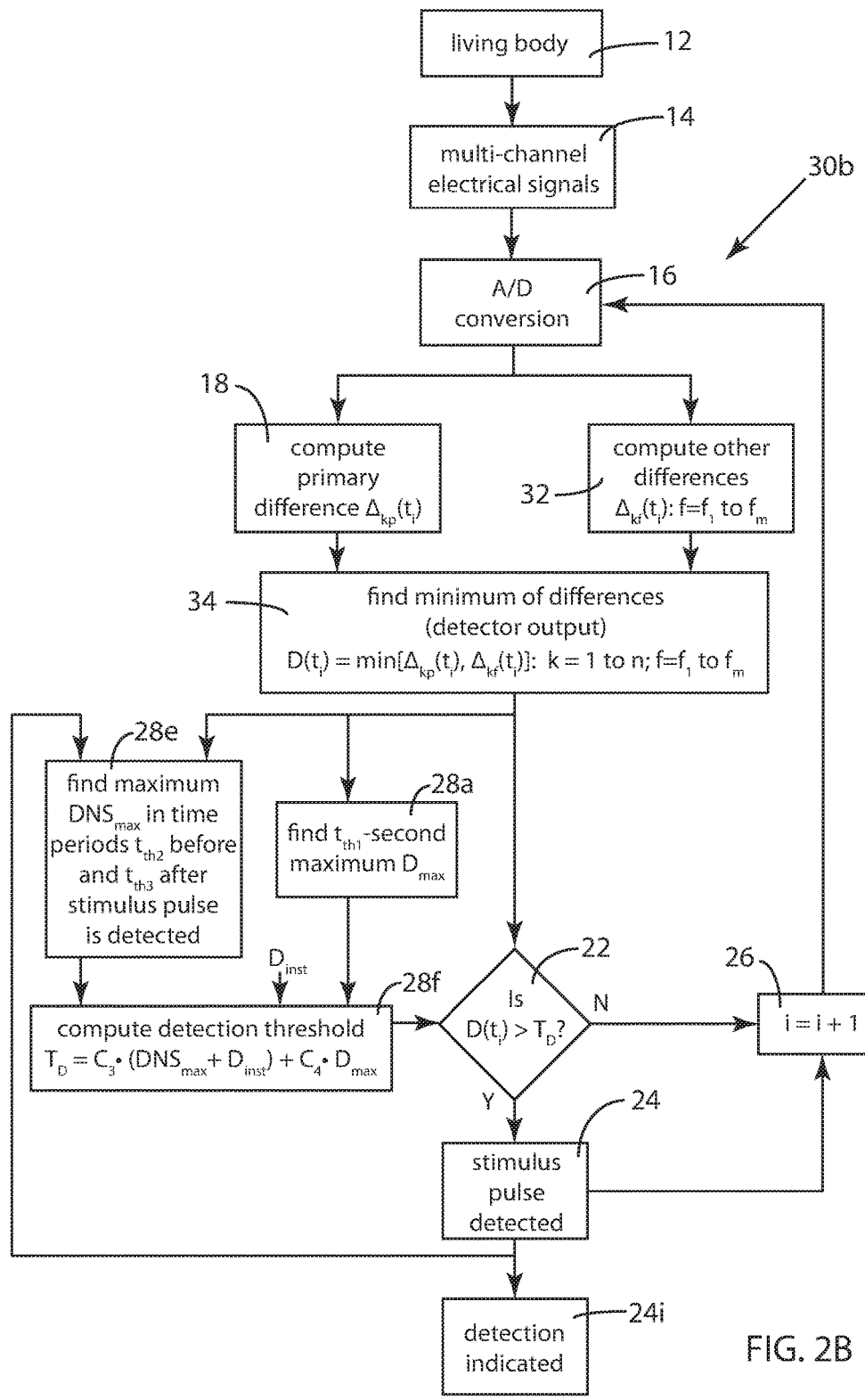
FIG. 2B is a schematic block diagram of the embodiment of FIG. 2 but including a second alternative method for determining the value of the detection threshold. This second alternative involves determining a maximum of non-stimulus local peaks during time periods both before and after a stimulus pulse is detected.

FIG. 2A is a block diagram of an alternative embodiment 30a to embodiment 30 of FIG. 2. Method embodiment 30a includes the alternative method for determining the value of the detection threshold $T_D$ from FIG. 1A, such alternative $T_D$ determination method comprising method steps 28c and 28d. In a similar fashion, method embodiment 30b in FIG. 2B is similar to embodiment 30 but with the alternative determination of detection threshold $T_D$ as illustrated in FIG. 1B, such alternative $T_D$ determination method comprising method steps 28a, 28e and 28f. Each of these method steps 28a-28e have been described above.

FIG. 3 is a partial schematic block diagram of an embodiment 50 which is a modification to the method embodiments 10, 10a, 10b, 30, 30a and 30b of FIGS. 1 through 2B in which indication at method step 24i of a stimulus pulse detection is suppressed for a suppression time period $t_S$ after a previous stimulus pulse has been detected at time $t_{sd}$=$t_{sdp}$ where $t_{sd}$ is the time of stimulus pulse detection and $t_{sdp}$ is the time of detection of the previous stimulus pulse. Such a time comparison is carried out in a method step 52. If the time of stimulus pulse detection $t_{sd}$ is greater than $t_{sdp}$+$t_S$, then the inventive method indicates that a stimulus pulse has been detected. The "Y" output in comparison step 52 is connected through a method step 52a in the block diagram to indicate that a new value for detection time $t_{sdp}$ is passed on to method step 52 when a stimulus pulse detection satisfies the conditional comparison of method step 52.

The purpose of such suppression is to ignore subsidiary local peaks in detector filter output $D(t_i)$ which are close in time to a stimulus pulse since such subsidiary local peaks occurring within time period $t_S$ after an occurrence of a stimulus pulse may cause false positive detections of stimulus pulses. The value for suppression time period $t_S$ is chosen to encompass the electrical-signal aftereffects which are caused by a stimulus pulse itself and to be short of the expected time of the next stimulus pulse. In the field of cardiology, the electrical-signal aftereffects are often referred to as pace tails.

FIG. 3A is a partial schematic block diagram of an embodiment 60 which is a modification to the method embodiments of FIGS. 1-2B in which a stimulus pulse is removed from one or more of the signals over a period of time $t_R$. The purpose of such removal in the field of cardiology, for example, conditions the signals from which a pacing pulse has been removed to allow a QRS detector to operate without interference from the pacing pulse. The process of removing pacing pulses is often referred to as blanking.

In method step 54, when a stimulus pulse is detected (informed by the block diagram connection 54a), the signals from which the stimulus pulse is to be removed are processed to remove the presence of the stimulus pulse over a time period $t_R$. The process is rapid and automatic, and thus time period $t_R$ may actually begin just prior to the detection time $t_{sd}$ and extend forward in time such that the aftereffects (pace tail) of the detected stimulus pulse will predominantly occur during time period $t_R$. All of the logic to carry out such removal is embedded in method step 54 which then provides signal outputs 56 for use by other systems. Typical values for removal time period $t_R$ may be on the order of 10 to 40 msec, but these exemplary values are not intended to be limiting.

It is anticipated in this invention that removal of stimulus pulses from one or more signals may be realized by removal from signals which are outputs from A/D conversion step 16 as illustrated in FIG. 3A or directly from one or more of the electrical signals 14 which are in analog form.

Figure 4:
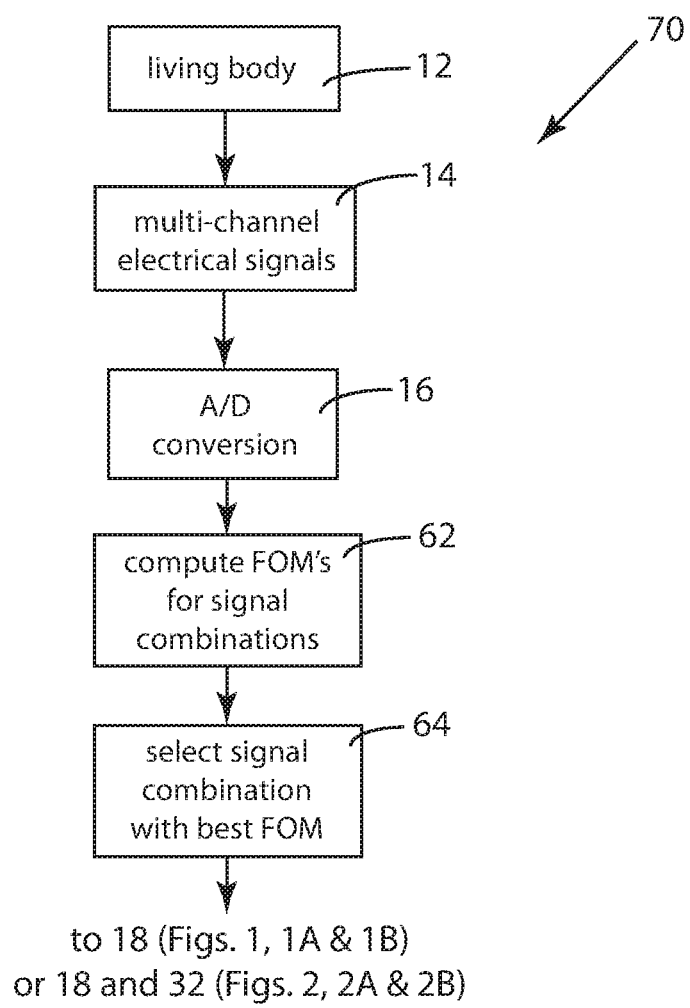
FIG. 4 is a partial schematic block diagram of a modification to the method embodiments of FIGS. 1-2B in which the two or more electrical signals are automatically selected using a figure-of-merit assessment of combinations of signals from a set of electrical signals derived from a living body. The method steps in FIG. 4 replace and add to method steps 12-16 in FIGS. 1-2B.

FIG. 4 is a partial schematic block diagram of an embodiment 70 of a modification to the method embodiments of FIGS. 1-2B in which the two or more signals are automatically selected using a figure-of-merit assessment 62 of combinations of signals from the set of electrical signals 14 derived from living body 12. Method steps 12 through 64 in FIG. 4 replace and add to method steps 12-16 in FIGS. 1-2B. In method step 62, various combinations of digital signals from method step 16 are selected, a figure-of-merit (FOM) is computed for each signal combination, and in method step 64 the combination with the best FOM is chosen from among multi-channel electrical signals 14 to be used in the inventive stimulus pulse detection method. Preferably all possible combinations of n signals 14 are considered in method step 62.

It is desirable for a stimulus pulse to be strong in an electrical signal used for detection, and further it is desirable that there be little or no errors in the time of detection of stimulus pulses in the selected electrical signals. For example, using a system in which the interval between stimulus pulses (pulse-to-pulse interval) is a constant, and evaluating signals over a fixed time period (e.g., 6 seconds) in which Q stimulus pulses occur, one useful FOM may be determined by: (1) computing the detector output and therefore final threshold $T_{DF}$ for all possible combinations of n signals; (2) computing the pulse-to-pulse intervals of detected stimulus pulses for all possible combinations of n signals and using the pulse-to-pulse intervals to form an interval variation term $I_{VARj}$ for the $j^{th}$ combination; and (3) computing FOM as the difference between the value of $T_{DF}$ for a signal combination and the sum of the absolute value of the variation of pulse-to-pulse intervals of detected stimulus pulses for that combination. If there are G possible combinations of signals, then $FOM_j = T_{DFj} - I_{VARj}$ for j=1 to G where the interval variation for the $j^{th}$ signal combination is represented by $V_{VARj} = sum[abs(di_{jq} - di_{jq-1})]$ where q=2 to Q and the value $di_{jq}$ is the $q^{th}$ pulse-to-pulse stimulus pulse detection time interval in the fixed time period of this determination. The value of FOM is higher for high values of $T_{DF}$ and low values of $I_{VAR}$; thus the best combination is the combination, in this case, having the highest value of FOM. Note that if a stimulus pulse is missed (not detected) in a combination, then the value of $I_{VAR}$ for that combination is penalized. In the field of cardiology, the relative sizes of the two terms in this FOM are satisfactory if $T_{DF}$ is given in microvolts and $I_{VAR}$ is given in milliseconds when the fixed period of time for automatic channel selection is about 6 seconds. The fixed time period of 6 seconds is not intended to be limiting. It is also possible in another situation and application that a relative weighting factor between the two terms of this FOM will be useful to make the automatic selection process appropriately sensitive.

One very significant feature of the inventive stimulus pulse detection method is its immunity to noise in the electrical signals such as powerline noise in which the frequency of the noise source is very stable. Referring again to FIG. 2, method step 32 contributes a set of m other differences $\Delta_{kf}(t_i)$ to set of differences already containing the primary differences $\Delta_{kp}(t_i)$. The parameters $f_1$ to $f_m$ represent the time differences in sample times for the various difference terms $\Delta_{kf}(t_i)$. For example, for 50 Hz powerline noise, the cycle time of the noise is 20 msec so that a difference term for f=20 will include essentially complete cancellation of any 50 Hz noise present in the signals. Thus, the inventive method for stimulus pulse detection includes an extremely straightforward and effective noise filter for 50 Hz powerline noise.

For 60 Hz noise, the most effective value for f is 16.667. If an integer value for f of 17 is used, the amount of 60 Hz noise which is admitted into the detector output is quite small. However, by determining values of signals $S_{kf}$ (t−16.667), or if necessary $S_{kf}$(t+16.667), by interpolation using neighboring values $S_{kf}$(t−16) and $S_{kf}$(t−17), or if necessary $S_{kf}$(t+16) and $S_{kf}$(t+17) of the corresponding sampled signal $S_k$, the amount of noise admitted into the detector output is essentially insignificant, and the extra computational load is minimal. Since powerline noise is often one of the most significant sources of electrical signal noise in such signals, this feature of the inventive filter provides a significant improvement in stimulus pulse detection.

If the sampling rate employed is evenly divisible by both 50 and 60, such as 1,200 sps, then no interpolation is required for broadly effective powerline noise filtering. 400 Hz is also a standard frequency for some systems, and a sampling rate 1,200 sps also yields an integer value for f of 3.

FIGS. 5A through 13B are time-plots illustrating the operation of exemplary embodiment 30 (see FIG. 2) of the inventive stimulus pulse detection method described herein, illustrating a single stimulus pulse detection. FIGS. 5A through 13B include time-plots, all of which are: (a) plots of cardiac signals measured in microvolts; (b) computed difference terms as described above, also measured in microvolts and all positive since the difference terms are all absolute values terms; or (c) detector outputs also measured in microvolts and all positive.

The multi-channel electrical signals 14 of this example are two intracardiac signals (n=2), designated Channel A as $S_1$ and Channel B as $S_2$, and these signals span an exemplary time period of 500 msec taken from within a much longer time period over which the inventive method was applied. The signals were sampled at 1,000 sps.

The time-plots of FIGS. 5A through 13B span two different time periods, 500 msec or 50 msec. The 50 msec time-plots each illustrates an expanded portion from a corresponding 500 msec time-plot. All of the 500 msec time-plots span the identical time period, and all of 50 msec time-plots span the identical 50 msec time period within the 500 msec time period. Because of the consistency of the time-plots being in microvolts versus time, none of the time-plots includes labels on the abscissa or ordinate axes. The identical 50 msec time periods of the expanded time-plots are all indicated by a pair of vertical dotted lines 80. Each time-plot includes a circle 82 which is centered around the point in the stream of digital data at which exemplary method embodiment 30 has detected a stimulus pulse.

FIGS. 5A and 5B are time-plots of 500 msec portions of exemplary digitized cardiac electrical signals 14 (Channel A and Channel B, respectively) derived from living body 12 of a human patient. Exemplary method embodiment 30 includes the following parameters: n=2, Channel A for k=1 and Channel B for k=2; p=1; m=2, $f_1$=17; $f_2$=20; $t_{th1}$=2 sec; and $C_1$=0.5. The source of the stimulus pulse was an external generator connected to the heart through a catheter for the purpose of an electrophysiological study.

FIGS. 6A and 6B are time-plots of 50 msec portions of the Channel A and Channel B digitized signals of FIGS. 5A and 5B, respectively, as indicated by vertical dotted lines 80.

Figure 7A:
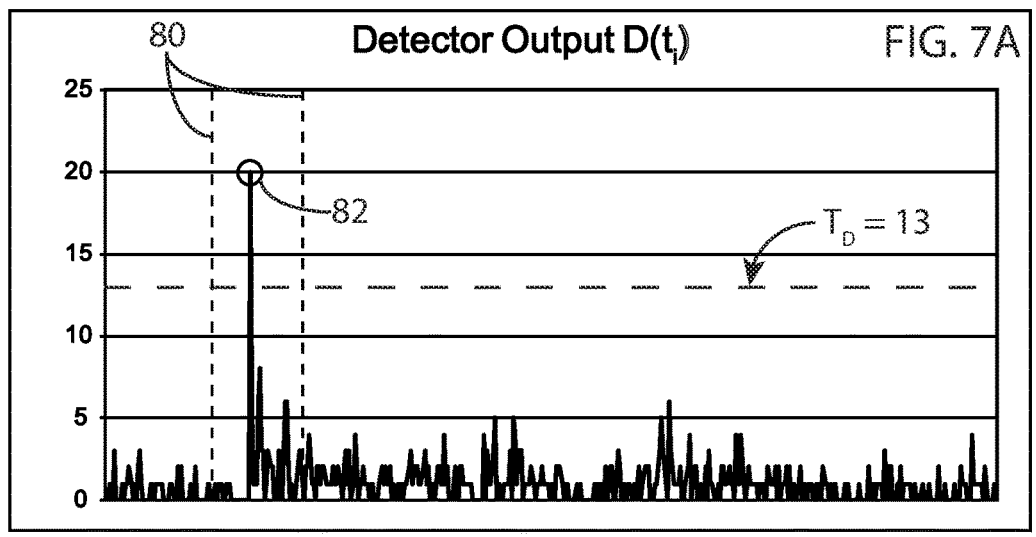
FIG. 7A is a time-plot of the detector output of an exemplary embodiment of the inventive method, computed from the electrical signals of FIGS. 5A and 5B. The time span of FIG. 7A is identical to that of FIGS. 5A and 5B.
Figure 7B:
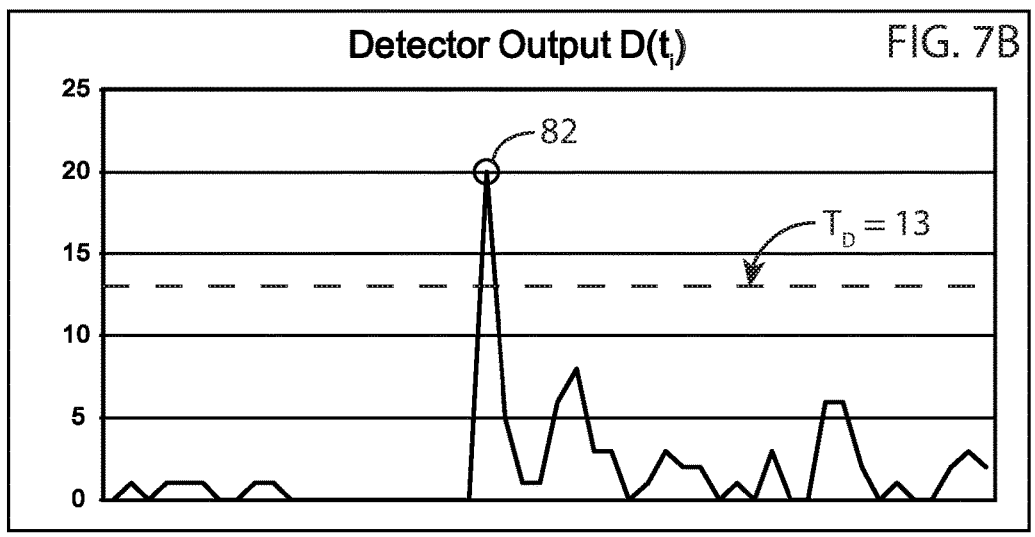
FIG. 7B is an expanded portion of the time-plot of FIG. 7A. The time span of FIG. 7B is indicated on FIG. 7A and is identical to the indicated time spans in FIGS. 5A and 5B.
Figure 11A:
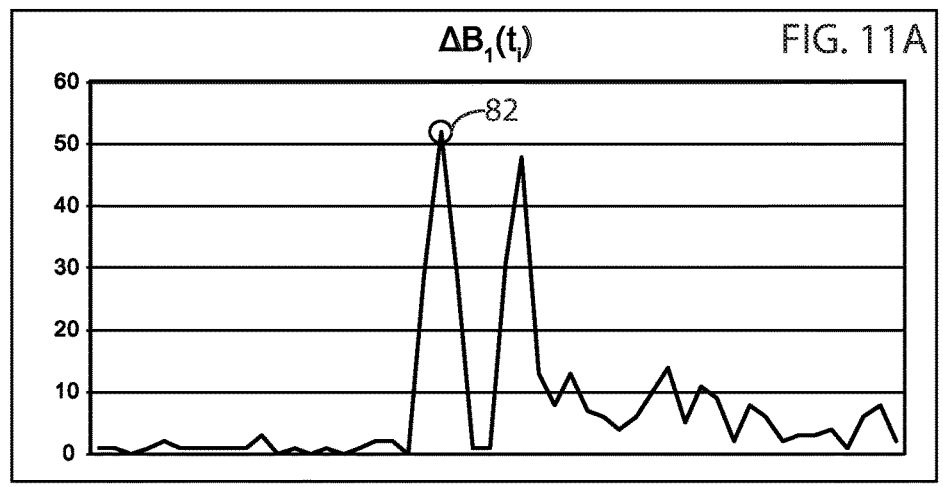
FIGS. 11A-11C are expanded time-plots of portions of the plots of FIGS. 10A-10C, respectively. The time spans of these plots are indicated on FIGS. 10A-10C with vertical dotted lines.
Figure 11B:
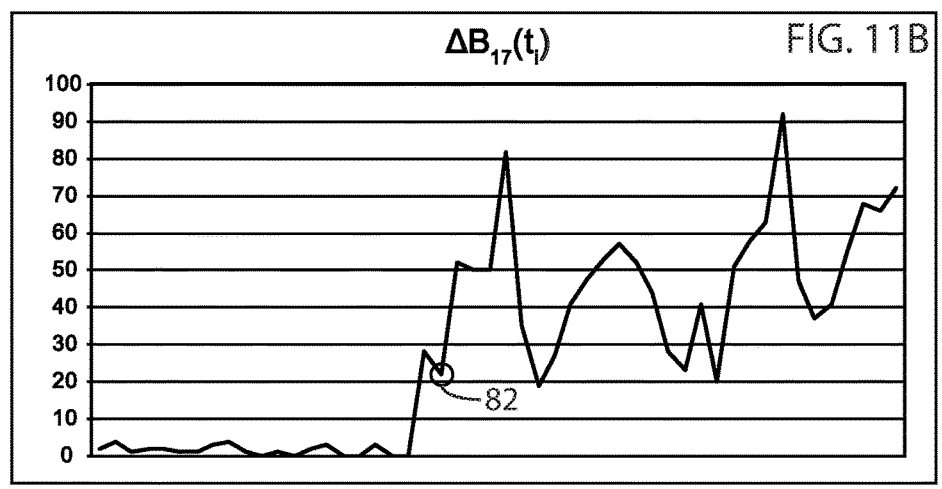
Figure 11C:
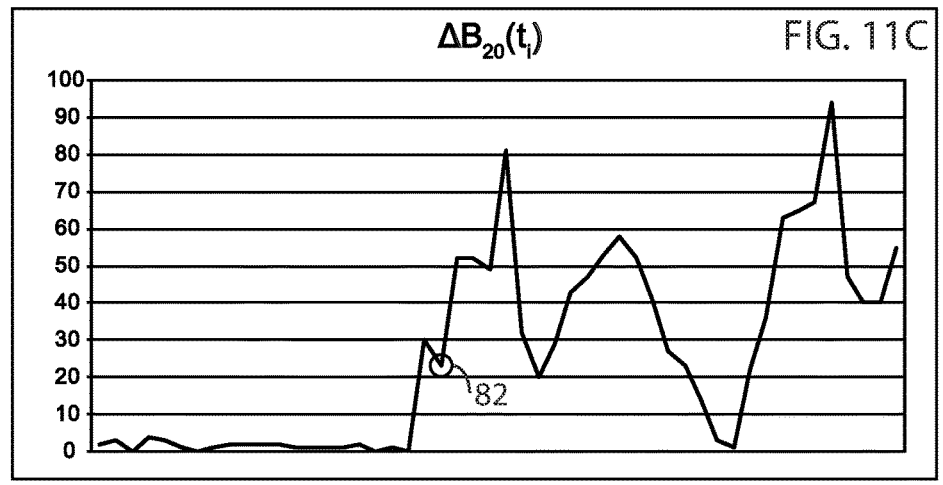

FIG. 7A is a time-plot of detector output $D(t_i)$ computed from the Channel A and Channel B signals of FIGS. 5A and 5B. The time span of FIG. 7A is identical to that of FIGS. 5A and 5B. The computations of method embodiment 30 are of necessity performed by suitable computational apparatus since the automatic detection of the inventive method will usually be carried out during a medical procedure which requires immediate knowledge of the occurrence of a stimulus pulse. FIG. 7B is a 50 msec expanded portion of the time-plot of FIG. 7A. Detection threshold $T_D$ was computed within method embodiment 30 to be $T_D=13$ as indicated on FIGS. 7A and 7B.

FIGS. 8A-8C and 10A-10C are 500 msec time-plots of the exemplary difference terms as indicated in such figures. These difference terms are interim values within method embodiment 30, computed from the signals of FIGS. 5A and 5B, respectively, as elements in the inventive stimulus pulse detection method as described in detail above. FIGS. 9A-9C and 11A-11C are 50 msec expanded portions from FIGS. 8A-8C and 10A-10C, respectively, as indicated on such figures.

During the 500 msec time span of the Channel A and Channel B signals shown in FIGS. 5A and 5B, respectively, the electrical signals contain a considerable number of signal-level variations which are larger than, or on the order of, the variations caused by the occurrence of the stimulus pulse. The inventive stimulus pulse detection method is able to determine which variation is caused by a stimulus pulse by exploiting the precise time coincidence of events in Channel A and Channel B and doing so with very little computational complexity.

FIGS. 12A-13B provide further illustration of method embodiment 30. The Channel A and Channel B signals of FIGS. 12A and 12B are the identical signals from FIGS. 5A and 5B but with a significant level of 60 Hz noise added numerically to illustrate the performance of the inventive stimulus pulse detection method in the presence of powerline noise. A comparison of FIGS. 12A and 12B with FIGS. 5A and 5B, respectively, clearly shows the effect of such added 60 Hz noise. 30 microvolt peak-to-peak noise was added to both Channel A and Channel B, and in addition, a 10 microvolt peak-to-peak $3^{rd}$ harmonic of the 60 Hz powerline noise was added to Channel B.

In the same computations with method embodiment 30 as were carried in for the example of FIGS. 5A-11C, the corresponding interim difference terms were computed, and from these the detector output $D(t_i)$ as shown in FIGS. 13A and 13B. In this powerline noise example, detection threshold $T_D$ was computed within method embodiment 30 to be $T_D=16$ as indicated on FIGS. 13A and 13B.

As with the example based on the digitized signals of FIGS. 5A and 5B, the Channel A and Channel B signals of FIGS. 13A and 13B contain a considerable number of signal-level variations which are larger than, or on the order of, the variations caused by the occurrence of the stimulus pulse, but such variations are now in signals which also include considerable levels of powerline noise. Again, the inventive stimulus pulse detection method is able to determine which variation is caused by a stimulus pulse by exploiting the precise time coincidence of events in Channel A and Channel B and doing so with very little computational complexity. As described above, the value of $f_1$ in this example is $f_1=17$. The integer 17 is close to the ideal value of 16.667 for filtering out 60 Hz noise (and all of its harmonics) and is shown by this example to be effective in doing so.

Even in situations in which there is little or no powerline noise, the inclusion of one or more other differences (in addition to the primary differences) as shown in the method embodiments 30, 30a, and 30b of FIGS. 2, 2A and 2B, respectively, adds performance to the stimulus pulse detection method of this invention. (In the examples described above, additional difference terms for $f_2=20$ were also included in these exemplary instances of method embodiment 30 even though 50 Hz noise was not present in the Channel A or Channel B signals.) Such other differences serve to help ensure the uniqueness of events for which detector output $D(t_i)$ is above detection threshold $T_D$. That is, since detector output $D(t_i)$ is the minimum of all of the difference terms, such other difference terms contribute differences to the computation of $D(t_i)$ such that when $D(t_i)$ is greater than detection threshold $T_D$, the likelihood that a coincident event has occurred is increased.

While the principles of this invention have been described in connection with specific embodiments, it should be understood clearly that these descriptions are made only by way of example and are not intended to limit the scope of the invention.

The invention claimed is:

1. A method for detecting a stimulus pulse by using two or more electrical signals derived from a living body, the method comprising:
    for each electrical signal, digitizing the signal with an analog-to-digital converter to produce a sampled signal $S_k$;
    for each signal $S_k$ at a sample time $t_i$, computing a primary difference $\Delta_{kp}(t_i)=abs[S_k(t_i)-S_k(t_{i-p})]$;
    determining the minimum value of all of the computed differences, such minimum being a detector output $D(t_i)$;
    comparing the detector output $D(t_i)$ with a detection threshold; and
    indicating that a stimulus pulse has been detected when the detector output $D(t_i)$ is above the detection threshold.

2. The stimulus pulse detection method of claim 1 wherein p is equal to 1.

3. The stimulus pulse detection method of claim 1 wherein p is equal to −1.

4. The stimulus pulse detection method of claim 1 further including the step of determining the detection threshold based on the maximum value $D_{max}$ of detector output $D(t_i)$ over a time period $t_{th1}$.

5. The stimulus pulse detection method of claim 4 wherein the detection threshold is a constant times $D_{max}$.

6. The stimulus pulse detection method of claim 4 further including the steps of:
    determining the maximum value $DNS_{max}$ of non-stimulus-pulse local peaks of detector output $D(t_i)$ in a period of time $t_{th2}$ before a detected stimulus pulse and a period of time $t_{th3}$ after a detected stimulus pulse;
    determining hardware-only noise $D_{inst}$ in the detector output $D(t_i)$; and
    computing the detection threshold as a first constant times the sum of $DNS_{max}$ and $D_{inst}$ plus a second constant times $D_{max}$.

7. The stimulus pulse detection method of claim 1 further including the steps of:
    determining the maximum value $DNS_{max}$ of non-stimulus-pulse local peaks of detector output $D(t_i)$ in a period of time $t_{th3}$ after a detected stimulus pulse; and
    computing the detection threshold as a constant plus $DNS_{max}$.

8. The stimulus pulse detection method of claim 1 further including the step of suppressing indication of additional stimulus pulse detections for a period of time $t_S$ after a stimulus pulse is detected.

9. The stimulus pulse detection method of claim 1 further including the step of removing a detected stimulus pulse from one of more of the signals.

10. The stimulus pulse detection method of claim 1 further including the step of automatically selecting the two or more electrical signals from a set of electrical signals derived from a living body.

11. The stimulus pulse detection method of claim 10 wherein automatically selecting the two or more electrical signals includes determining a figure-of-merit of combinations of electrical signals from the set of electrical signals.

12. The stimulus pulse detection method of claim 1 further including for each sampled signal $S_k$ at sample time $t_i$, computing one or more other differences $\Delta_{kf}(t_i) = \text{abs}[S_k(t_i) - S_k(t_{i-f})]$, each other difference using a unique value for f and such other differences being computed prior to determining the minimum value of all of the computed differences.

13. The stimulus pulse detection method of claim 12 wherein p is equal to 1 and all values of f are positive.

14. The stimulus pulse detection method of claim 13 wherein at least one of the values of f is a non-integer value and the values of $S_k(t_{i-f})$ are determined by interpolation using neighboring values of the corresponding sampled signal $S_k$.

15. The stimulus pulse detection method of claim 13 wherein all values of f are positive integers.

16. The stimulus pulse detection method of claim 12 wherein p is equal to −1 and all values of f are negative.

17. The stimulus pulse detection method of claim 16 wherein at least one of the values of f is a non-integer value and the values of $S_k(t_{i-f})$ are determined by interpolation using neighboring values of the corresponding sampled signal $S_k$.

18. The stimulus pulse detection method of claim 16 wherein all values of f are negative integers.

19. The stimulus pulse detection method of claim 12 further including the step of determining the detection threshold based on the maximum value $D_{max}$ of the detector output $D(t_i)$ over a time period $t_{th1}$.

20. The stimulus pulse detection method of claim 19 wherein the detection threshold is a constant times $D_{max}$.

21. The stimulus pulse detection method of claim 19 further including the steps of:
determining the maximum value $DNS_{max}$ of non-stimulus-pulse local peaks of detector output $D(t_i)$ in a period of time $t_{th2}$ before a detected stimulus pulse and a period of time $t_{th3}$ after a detected stimulus pulse;
determining hardware-only noise $D_{inst}$ in the detector output $D(t_i)$; and
computing the detection threshold as a first constant times the sum of $DNS_{max}$ and $D_{inst}$ plus a second constant times $D_{max}$.

22. The stimulus pulse detection method of claim 12 further including the steps of:
determining the maximum value $DNS_{max}$ of non-stimulus-pulse local peaks of detector output $D(t_i)$ in a period of time $t_{th2}$ before a detected stimulus pulse and a period of time $t_{th3}$ after a detected stimulus pulse;
determining hardware-only noise $D_{inst}$ in the detector output $D(t_i)$; and
computing the detection threshold as a first constant times the sum of $DNS_{max}$ and $D_{inst}$ plus a second constant times $D_{max}$.

23. The stimulus pulse detection method of claim 12 further including the steps of:
determining the maximum value $DNS_{max}$ of non-stimulus-pulse local peaks of detector output $D(t_i)$ in a period of time $t_{th3}$ after a detected stimulus pulse; and
computing the detection threshold as a constant plus $DNS_{max}$.

24. The stimulus pulse detection method of claim 12 wherein at least one f value is chosen to filter out noise at a frequency selected from the group consisting of 50 Hz, 60 Hz and 400 Hz.

25. The stimulus pulse detection method of claim 12 wherein the digitizing of the two or more electrical signals is done at a sampling rate which is evenly divisible by each of the one or more values of f.

26. The stimulus pulse detection method of claim 12 further including the step of suppressing indication of additional stimulus pulse detections for a period of time $t_S$ after a stimulus pulse is detected.

27. The stimulus pulse detection method of claim 12 further including the step of removing a detected stimulus pulse from one or more of the signals.

28. The stimulus pulse detection method of claim 12 further including the step of automatically selecting the two or more electrical signals from a set of electrical signals derived from a living body.

29. The stimulus pulse detection method of claim 28 wherein automatically selecting the two or more electrical signals includes determining a figure-of-merit of combinations of electrical signals from the set of electrical signals.

* * * * *